US009202009B2

(12) United States Patent
Seike et al.

(10) Patent No.: US 9,202,009 B2
(45) Date of Patent: Dec. 1, 2015

(54) DIAGNOSTIC SUPPORT APPARATUS FOR DIABETES AND COMPUTER PROGRAM PRODUCT

(75) Inventors: Masayoshi Seike, Kobe (JP); Yoshihiko Tashima, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 0 days.

(21) Appl. No.: 12/644,863

(22) Filed: Dec. 22, 2009

(65) Prior Publication Data

US 2010/0161299 A1  Jun. 24, 2010

(30) Foreign Application Priority Data

Dec. 22, 2008  (JP) ................................. 2008-325875

(51) Int. Cl.
*G01N 33/48* (2006.01)
*G01N 33/50* (2006.01)
*G01N 31/00* (2006.01)
*G06F 19/00* (2011.01)
*G06F 19/20* (2011.01)
*G06F 19/12* (2011.01)
*G06F 19/24* (2011.01)

(52) U.S. Cl.
CPC ............ *G06F 19/3437* (2013.01); *G06F 19/12* (2013.01); *G06F 19/20* (2013.01); *G06F 19/24* (2013.01)

(58) Field of Classification Search
None
See application file for complete search history.

(56) References Cited

U.S. PATENT DOCUMENTS

2005/0234311 A1  10/2005  Kouchi et al.
2006/0277015 A1  12/2006  Kouchi et al.

FOREIGN PATENT DOCUMENTS

JP   2005-267042 A   9/2005
JP   2005-353050     12/2005

OTHER PUBLICATIONS

Parker et al. Robust H glucose control in diabetes using a physiological model. AIChE Journal, 2000, vol. 46, pp. 2537-2549.*
Naito et al. Construction of a simulation model of diabetes for pathophysiological analysis using E-Cell system. Genome Informatics, 2002, vol. 123, pp. 478-479.*
Man et al. The oral glucose minimal model: Estimation of insulin sensitivity from a meal test. IEEE Transactions on Biomedical Engineering, vol. 49, 2002, pp. 419-429.*

(Continued)

*Primary Examiner* — Russell S Negin
(74) *Attorney, Agent, or Firm* — Sughrue Mion, PLLC

(57) ABSTRACT

The present invention is to present a diagnostic support apparatus for diabetes including a diagnostic support information generating unit which generates diagnostic support information of a patient based on a biological model for reproducing a pseudo-response which simulates a result of a glucose tolerance test for the patient. The biological model comprises a plurality of simulated organ blocks which are configured in such manner that inflow and outflow of glucose and/or inflow and outflow of insulin are reciprocally produced between each of the simulated organ blocks. The plurality of the simulated organ blocks respectively calculate at least one of a cumulative quantity and a concentration of glucose and/or at least one of a cumulative quantity and a concentration of insulin in the respective simulated organ blocks, based on a quantity of inflow and outflow of glucose and/or a quantity of inflow and outflow of insulin in the respective simulated organ blocks.

15 Claims, 11 Drawing Sheets

(56) References Cited

OTHER PUBLICATIONS

Bergman et al. Physiologic evaluation of factors controlling glucose tolerance in man. Journal of Clinical Investigation, vol. 68, 1981, pp. 1456-1467.*

High-density lipoprotein: synthesis of lipoprotein complexes. Encyclopedia Britannica, Inc. Obtained online on May 28, 2014, two pages.*

European Search Report issued Jul. 3, 2013 for European Application No. 09 01 5715.

Man, Chiara Dalla et al., "Meal Simulation Model of the Glucose-Insulin System", IEEE Transactions on Biomedical Engineering, Oct. 1, 2007, pp. 1740-1749, vol. 54, No. 10, IEEE Service Center, Piscataway, NJ, USA.

Cobelli, Claudio, et al., "Diabetes: Models, 1-15 Signals, and Control", IEEE Reviews in Biomedical Engineering, Jan. 1, 2009, pp. 54-96, vol. 2, IEEE, USA.

* cited by examiner

FIG. 11

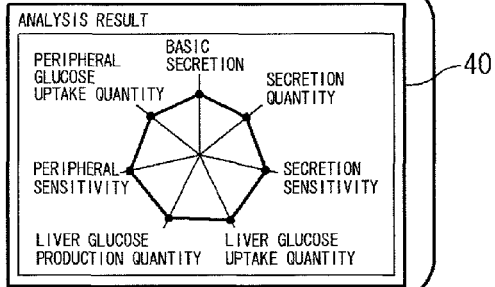

[NORMAL PROFILE EXAMPLE]

BALANCED OUTPUT PROFILE REPRESENTING NORMAL CONDITION WITH SMALL AXIS VALUE MEANING CORRESPONDING FUNCTION DECLINE

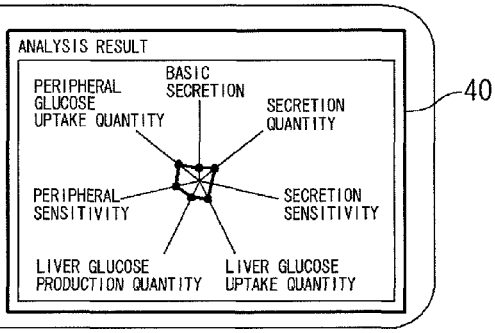

[SECRETION DEFICIENCY TYPE]

PATHOLOGICAL CONDITION OF DIFFICULT BLOOD GLUCOSE CONTROL WITH ORAL MEDICINE OTHER THAN SU DRUG

RECOMMENDED DRUG
[**、、**]

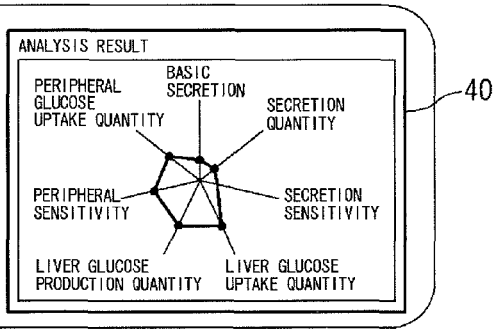

[SLIGHT SECRETION DEFICIENCY TYPE]

APPROPRIATE PATHOLOGICAL CONDITION FOR GLINIDE DRUG

RECOMMENDED DRUG
[**、*、]

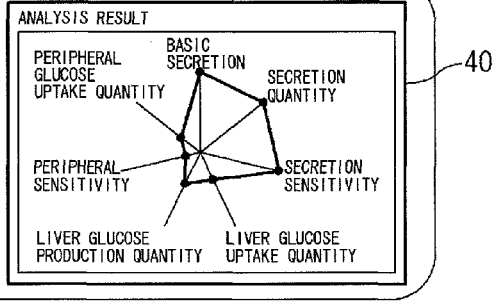

[RESISTIVITY TYPE]

APPROPRIATE PATHOLOGICAL CONDITION FOR INSULIN RESITIVITY IMPROVING DRUG

RECOMMENDED DRUG
[**、、**]

DIAGNOSTIC SUPPORT APPARATUS FOR DIABETES AND COMPUTER PROGRAM PRODUCT

BACKGROUND OF THE INVENTION

1. Field of the Invention

The present invention relates to an apparatus used for diabetes diagnostic support, and a computer program product.

2. Description of the related art

As a system used for diabetes diagnostic support, one is disclosed in, for example, US Patent Publication No. 2006-277015.

In US Patent Publication No. 2006-277015, a system includes a biological model in which a function of a biological organ is represented by a mathematical model, and the function of the biological organ is simulated by a computer with this biological model.

The biological model according to US Patent Publication No. 2006-277015 includes four blocks: a pancreas block representing a function of pancreas, an insulin kinetic block representing a function of insulin kinetics, a peripheral tissue block representing a function of a peripheral tissue, and a liver block representing a function of a liver. A biological body is simulated by these blocks.

In the biological model, the pancreas block obtains an insulin secretion rate based on a blood glucose level provided by the peripheral tissue block. The insulin secretion rate is provided to the liver block. Further, the liver block obtains net glucose release from the liver and insulin having passed the liver based on glucose absorption from outside, the blood glucose level provided by the peripheral tissue block, and the insulin secretion rate provided by the pancreas block. The net glucose release from the liver is provided to the peripheral tissue block, and the insulin having passed the liver is provided to the insulin kinetic block.

Further, the insulin kinetic block obtains concentrations of blood insulin and peripheral tissue insulin based on the insulin having passed the liver provided by the liver block. Although the blood insulin concentration is not provided to the other blocks, the peripheral tissue insulin concentration is provided to the peripheral tissue block. The peripheral tissue block obtains the blood glucose level based on the net glucose release from the liver block and the peripheral tissue insulin concentration from the insulin kinetic block. The blood glucose level is provided to the pancreas block and the liver block.

For accurately generating a pathological condition analysis index for diabetes based on the biological model reproducing pseudo-response which simulates a result of a glucose tolerance test for an individual patient, a cumulative quantity or a concentration of glucose/insulin which reflects a balance in respective organs of the patient is important. This is because an uptake rate (consumption rate) of glucose/insulin which is to be the pathological condition analysis index for diabetes depends on the cumulative quantity or a concentration of glucose/insulin in respective organs.

However, in such the biological model according to US Patent Publication No. 2006-277015, plural simulated organ blocks configuring the biological model are configured by units of organs in which a glucose/insulin concentration is to be obtained, but the respective plural simulated organs are not purposed to obtain the cumulative quantity or the concentration of glucose/insulin in consideration of the balance.

Further, for obtaining the cumulative quantity or the concentration of glucose/insulin in consideration of the balance in the respective simulated organ blocks, it is required to balance inflow and outflow of glucose/insulin in each of a plurality of the simulated organ blocks configuring the biological model. Although glucose and insulin are reciprocated between each block configuring the biological model in US Patent Publication No. 2006-277015, each block focus only on representing functions of the corresponding organ. It is not purposed to balance inflow and outflow of glucose/insulin in each block and obtain the cumulative quantity or the concentration of glucose/insulin.

For example, the liver block in US Patent Publication No. 2006-277015 just calculates a quantity of glucose released based on the inflow glucose one-sidedly, but a balance of inflow and outflow of glucose with respect to the liver block is not considered. Therefore, it is impossible to obtain the cumulative quantity or the concentration of glucose in the liver block in consideration of balance. Further, the peripheral tissue block of US Patent Publication No. 2006-277015 just calculates blood glucose level (glucose quantity in blood plasma) based on a glucose release quantity from the liver block. It is not purposed to obtain the cumulative quantity or the concentration of glucose of the peripheral tissue block itself in consideration of balance.

Meanwhile, the insulin kinetic block of US Patent Publication No. 2006-277015 calculates an insulin concentration but does not reflect the balance.

BRIEF SUMMARY OF THE INVENTION

The scope of the present invention is defined solely by the appended claims, and is not affected to any degree by the statements within this summary.

A first aspect of the present invention is a diagnostic support apparatus for diabetes comprising a diagnostic support information generating unit which generates diagnostic support information of a patient based on a biological model for reproducing a pseudo-response which simulates a result of a glucose tolerance test for the patient, wherein the biological model comprises a plurality of simulated organ blocks which are configured in such manner that inflow and outflow of glucose and/or inflow and outflow of insulin are reciprocally produced between each of the simulated organ blocks, and wherein the plurality of the simulated organ blocks respectively calculate at least one of a cumulative quantity and a concentration of glucose and/or at least one of a cumulative quantity and a concentration of insulin in the respective simulated organ blocks, based on a quantity of inflow and outflow of glucose and/or a quantity of inflow and outflow of insulin in the respective simulated organ blocks.

A second aspect of the present invention is a diagnostic support apparatus for diabetes comprising a diagnostic support information generating unit which generates diagnostic support information of a patient based on a biological model for reproducing pseudo-response which simulates a result of a glucose tolerance test for the patient, wherein the biological model comprises an intestine block in which a glucose tolerance quantity in the glucose tolerance test is provided as exogenous glucose quantity from outside of the biological model, and wherein the intestine block calculates an exogenous glucose inflow rate based on the exogenous glucose quantity.

Further, a third aspect of the present invention is a computer program product, comprising:

a computer readable medium, and a software instructions, on the computer readable medium, for enabling the computer to perform an operation of generating a diagnostic support information for a patient based on a biological model reproducing pseudo-response which simulates a result of a glucose tolerance test for the patient, wherein the biological model comprises a plurality of simulated organ blocks in which inflow and outflow of glucose and/or inflow and outflow of insulin are produced reciprocally between each of the simulated organ blocks, and wherein the plurality of the simulated organ blocks respectively calculate at least one of a cumulative quantity and a concentration of glucose and/or at least one of a cumulative quantity and a concentration of insulin in the respective simulated organ blocks, based on a quantity of inflow and outflow of glucose and/or a quantity of inflow and outflow of insulin in the respective simulated organ blocks.

BRIEF DESCRIPTION OF THE DRAWINGS

FIG. 11 is a diagram showing outputted diagnostic support information.

DETAILED DESCRIPTION OF THE INVENTION

Hereinafter, embodiments of the present invention are explained with reference to figures attached hereto.

Figure 1:
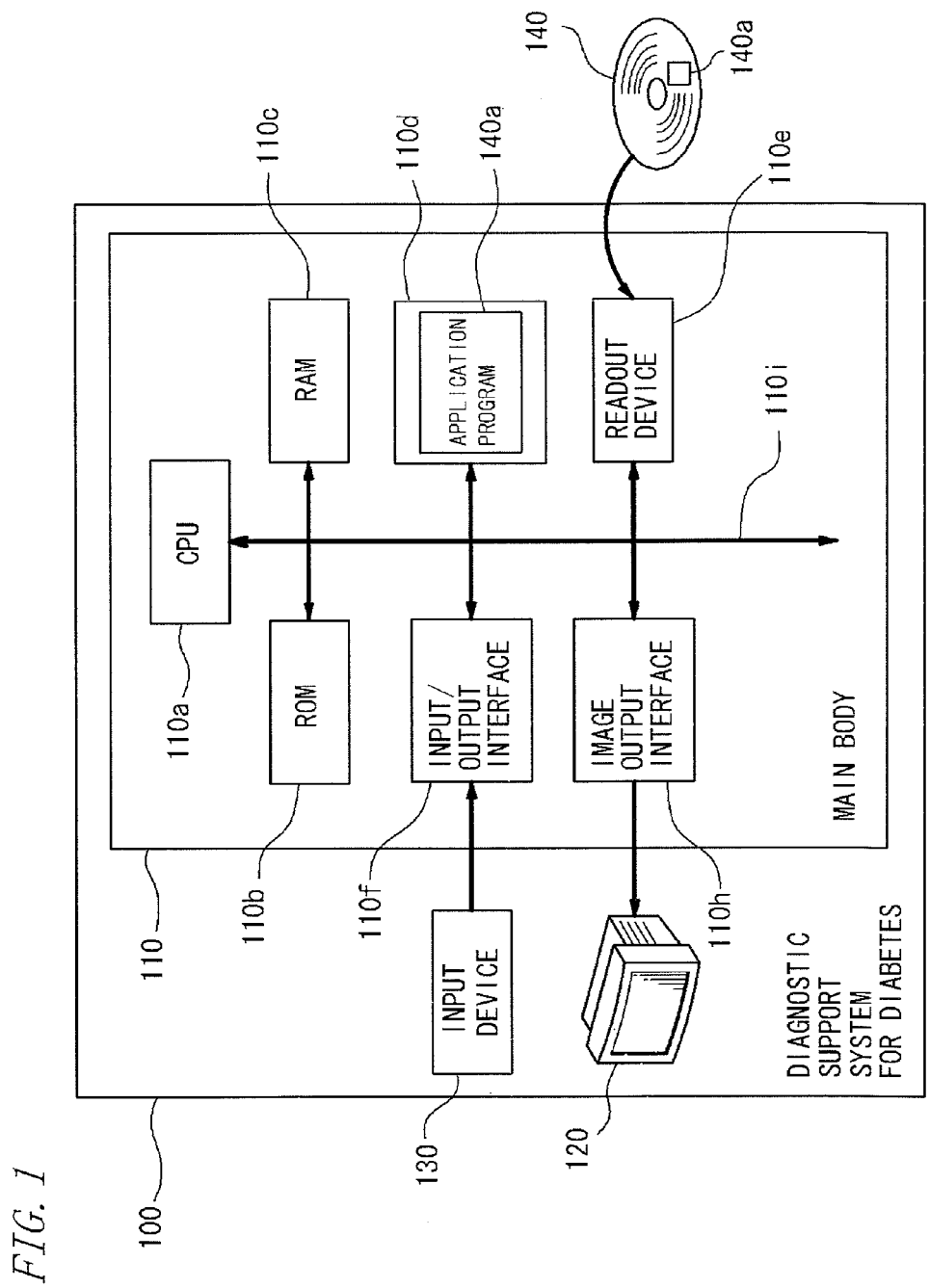
FIG. 1 is a hardware configuration diagram of a diagnostic support system for diabetes.

FIG. 1 is a block diagram showing a hardware configuration of a diagnostic support system for diabetes (hereinafter also simply referred to as "system") according to one of embodiments of the present invention. A system 100 according to the present embodiment is configured by a computer which mainly includes a main body 110, a display 120, and an input device 130. The main body 110 mainly includes CPU 110$a$, ROM 110$b$, RAM 110$c$, a hard disk 110$d$, a readout device 110$e$, an input-output interface 110$f$, and a image output interface 100$h$. The CPU 110$a$, the ROM 110$b$, the RAM 110$c$, the hard disk 110$d$, the readout device 110$e$, the input-output interface 110$f$, and the image output interface 110$h$ are connected and capable of data communication by a bus 110$i$.

The CPU 110$a$ is capable of executing a computer program memorized in the ROM 110$b$ and a computer program loaded in the RAM 110$c$. Respective function blocks described later are carried out by the CPU 110$a$ executing an application program 140$a$ described later, and thereby the computer functions as the system 100. The ROM 110$b$ includes a mask ROM, PROM, EPROM, EEPROM, and others, and records the computer program executed by the CPU 110$a$, data used for this, and others.

The RAM 110$c$ includes SRAM, DRAM, or others. The RAM 110$c$ is used for reading out the computer program recorded in the ROM 110$b$ and the hard disk 110$d$. It is also used as a work area of the CPU 110$a$ when these computer programs are executed. In the hard disk 110$d$, various computer programs for causing the CPU 110$a$ to execute such as an operating system and an application program, and data used for executing the computer programs are installed. The application program 140$a$ described later is also installed in this hard disk 110$d$.

The readout device 110$e$ includes a flexible disk drive, a CD-ROM drive, DVD-ROM drive, and others. It is capable of reading out a computer program or data which are recorded in a portable recording medium 140. Further, in the portable recording medium 140, the application program 140$a$ for causing the computer to function as a system of the present invention is stored. It is possible that the computer reads out the application program 140$a$ related to the present invention from the portable recording medium 140 and installs the application program 140$a$ in the hard disk 110$d$.

The application program 140$a$ is not only provided by the portable recording medium 140 but also through an electric communication line from an external device which is communicably connected to the computer by the electric communication line (wired or wireless). It is possible that, for example, the application program 140$a$ is stored in a hard disk of a server computer on the internet, and this server computer is accessed by the computer, the computer program is downloaded and installed in the hard disk 110$d$. Further, in the hard disk 110$d$, there is installed an operating system, providing a graphical users interface environment, such as Windows (trademark) manufactured and soled by U.S. Microsoft Corporation. In the following explanation, the application program 140$a$ according to the present embodiment is to operate on the operating system.

The input-output interface 110$f$ includes, for example, a serial interface such as USB, IEEE1394, and RS-232C; a parallel interface such as SCSI, IDE, and IEEE1284; and an analog interface including D/A converter, A/D converter and others. An input device 130 including a keyboard and a mouse is connected to the input-output interface 110$f$. It is possible that the user inputs data in the computer 100$a$ by using the input device 130. A display 120 including LCD or CRT, and others is connected to the image output interface 110$h$. Image signals in response to image data which are provided by the CPU 110$a$ are outputted on the display 120. The display 120 displays images (screen) in response to the inputted image signals.

[Biological Model in the Present System]

The present system 100 generates an index used for analyzing pathological conditions associated with a patient's diabetes based on a biological model M which reproduces pseudo-responses simulating results of a glucose tolerance test such as oral glucose tolerance test (OGTT), and the system 100 generates/outputs diagnostic support information associated with the diabetes. Hereinafter, a biological model in the present system 100 will be described and subsequently the other functions of the system 100 are described. As a glucose tolerance test, there has been a test, in which glucose is taken in orally, such as oral glucose tolerance test (OGTT) and metal test (MT).

The results of a glucose tolerance test include, for example, glucose concentration measured through blood drawing (hereinafter referred to as "blood drawing glucose concentration") and/or insulin concentration measured through blood drawing (hereinafter referred to as "blood drawing insulin concentration").

Figure 2:
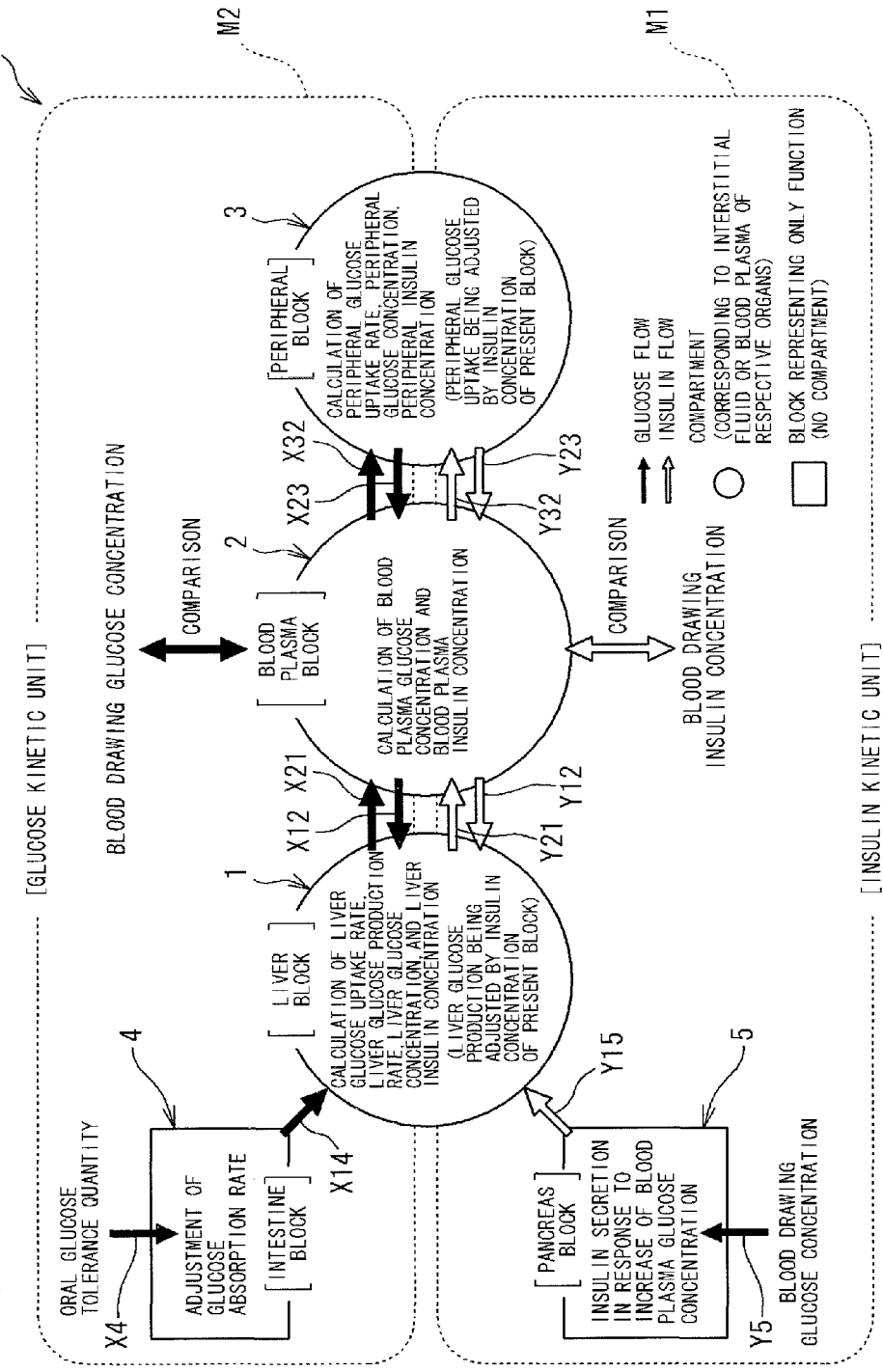
FIG. 2 is an overall configuration diagram of a biological model.

As shown in FIG. 2, the biological model M has plural simulated organ blocks 1, 2, 3, 4, and 5 which simulate patient's organs (including all organs and sites of the biological body). These blocks 1 to 5 describe the organ functions as mathematical models. The simulated organ blocks include a simulated liver block 1 simulating a liver (hereinafter referred to as "liver block"), a simulated blood plasma block 2 simulating a blood plasma (hereinafter referred to as "blood plasma block"), a simulated peripheral block 3 simulating a peripheral tissue (hereinafter referred to as "peripheral block"), a simulated intestine block 4 simulating an intestine (hereinafter referred to as "intestine block"), and a simulated pancreas block 5 simulating a pancreas (hereinafter referred to as "pancreas block").

The biological model M has a basic structure (structure shown as a block diagram in FIGS. 2 to 4) which is common to respective patients. Respective blocks 1 to 5 of the biological model M have a value common to the respective patients (fixed parameter) and a value inherent to an individual patient (a setup parameter and a variable parameter calculated from a fixed parameter). When the biological model M is generated, the variable parameter inherent to the individual patient is searched and adjusted so as to reproduce the blood drawing glucose concentration and the blood drawing insulin concentration being the result of the oral glucose tolerance test (OGTT) and the biological model adapted to the individual patient is generated. The variable parameter is not limited to one exemplified in the present embodiment. A part of the fixed parameter and the setup parameter in the present embodiment may be as a variable parameter.

In addition, among the simulated organ blocks 1 to 5, in a case where only the liver block 1, the blood plasma block 2, and the peripheral block 3 are generally referred, they are referred to as "first simulated organ block". In a case where only the intestine block 4 and the pancreas block 5 are generally referred, they are referred to as "second simulated organ block". As described later, an expression of organ is different among the first simulated organ blocks 1, 2, and 3 and the second simulated organ blocks 4 and 5.

Further, the biological model M which is generated in the present system 100 and used for the diagnostic support for the patient represents flows of glucose and insulin in the respective simulated organ blocks 1 to 5. The biological model M is largely divided into an insulin kinetic unit M1 showing an insulin flow and a glucose kinetic unit M2 showing a glucose flow. To the insulin kinetic unit M1, a function associated with insulin of the liver block 1, a function associated with insulin of the blood plasma block 2, a function associated with the peripheral block 3, and the pancreas block 5 belong. To the glucose kinetic unit M2, a function associated with glucose of the liver block 1, a function associated with glucose of the blood plasma block 2, a function associated with glucose of the peripheral block 3, and the intestine block 4 belong.

The liver block 1, the blood plasma block 2, and the peripheral block 3 being the first simulated organ blocks represent not only functions of organs (liver, blood plasma, peripheral tissue) but also interstitial fluid or blood plasma which is a carriage/cumulation medium of glucose and insulin in the respective organs (liver, blood plasma, peripheral tissue). Specifically, there is employed compartment model as the first simulated organ blocks 1, 2, and 3, in which a glucose balance and an insulin balance among the blocks are calculated and an cumulative state of glucose and insulin is calculated per first simulated organ blocks 1, 2, and 3. In other words, in the first simulated organ blocks 1, 2, and 3, inflow/outflow of glucose and insulin in and out the interstitial fluid or the blood plasma and uptake/disappearance in the organs are represented, and cumulative quantity of glucose and insulin in the interstitial fluid or the blood plasma of the respective organs is calculated. Thus, in the first simulated organ blocks 1, 2, and 3, transfer of glucose and insulin in the interstitial fluid and the blood plasma, accompanying a blood circulation is represented. However, with respect to an organ, it is not limited to the above described organs, but other organs may be included.

The liver block 1 is designed to represent a cumulative quantity (concentration) and others of glucose and insulin in an interstitial fluid of a liver, based on inflow and outflow of glucose and insulin to and from the interstitial fluid in the liver, and quantity of increase and decrease from the interstitial fluid of the liver due to a liver function (liver glucose uptake/liver glucose production).

As shown in FIG. 2, in the liver block 1, there are a glucose inflow X14 from the intestine block 4, a glucose inflow X12 from the blood plasma block 2, and a glucose outflow X21 to the blood plasma block 2. Further, in the liver block 1, there are an insulin inflow Y15 from the pancreas block 5, an insulin inflow Y12 from the blood plasma block 2, and an insulin outflow Y21 to the blood plasma block 2.

Further, the blood plasma block 2 is designed to represent a cumulative quantity (concentration) and others of glucose and insulin in a blood plasma based on inflow and outflow of glucose and insulin to and from the blood plasma. As shown in FIG. 2, in the blood plasma block 2, there are a glucose inflow X21 from the liver block 2, a glucose inflow X23 from the peripheral block 3, a glucose outflow X12 to the liver block 2, and a glucose outflow X32 to the peripheral block 3. Further, in the blood plasma block 2, there are an insulin inflow Y21 from the liver block 1, an insulin inflow Y23 from the peripheral block 3, and a glucose outflow Y12 to the liver block 1, and a glucose outflow Y32 to the peripheral block.

Further, the peripheral block 3 mainly simulates muscle/fat among body organs of a patient. However, as a peripheral tissue, it may be a tissue (including a glucose digesting function of the intestine and the pancreas) capable of digesting glucose except for the liver block and the peripheral block. The peripheral block 3 is designed to represent a cumulative quantity (concentration) and others of glucose and insulin in an interstitial fluid of a periphery based on inflow and outflow of glucose and insulin to and from the interstitial fluid in the peripheral tissue, and quantity of increase and decrease from interstitial fluid of the periphery due to a periphery function (peripheral glucose uptake).

As shown in FIG. 2, in the peripheral block 3, there are a glucose inflow X32 from the blood plasma block 2 and a glucose outflow X23 to the blood plasma block 2. Further, in the peripheral block 3, there are an insulin inflow Y32 from the blood plasma block and an insulin outflow Y23 to the blood plasma block.

In the intestine block 4 and the pancreas block 5 which are the second simulated organ block, there are no mutual inflow and outflow of glucose and insulin between blocks such as the first simulated organ blocks 1, 2, and 3 because they do not represent the interstitial fluid or the blood plasma. They are configured as a flow model for flowing glucose or insulin out to the liver block 1.

For example, in a case where predetermined glucose tolerance X4 is orally administered to the intestine block 4, the intestine block 4 adjusts a glucose absorption rate in the intestine, adjusts a dosage (speed) of exogenous glucose to the liver block 1 (the first simulated organ block), and carries out an exogenous glucose outflow X14 to the liver block 1. However, the intestine block 4 does not receive the glucose inflow from the liver block 1. In other words, the intestine block 4 represents not the glucose cumulative quantity in the interstitial fluid of the intestine but a function of the intestine being glucose absorption in the intestine.

Further, the pancreas block 5 secrets insulin in response to increase of blood plasma glucose concentration in the blood plasma block 2 and carries out insulin outflow Y15 (insulin secretion) to the liver block 1. However, the pancreas block 5 does not receive insulin inflow from the liver block 1 or the blood plasma block 2. In other words, the pancreas block 5 represents not insulin cumulative quantity in the interstitial fluid of the pancreas but a function of pancreas being insulin secretion in the pancreas.

In addition, inflow and outflow of glucose and insulin in the blocks 1 to 5 are received and given in terms of a common unit dimensional value being a glucose inflow rate or an insulin inflow rate. Therefore, it is easy to compute a balance between inflow and outflow of glucose and insulin among the respective blocks.

[Insulin Kinetic Unit and Glucose Kinetic Unit of Biological Model]

Figure 3:
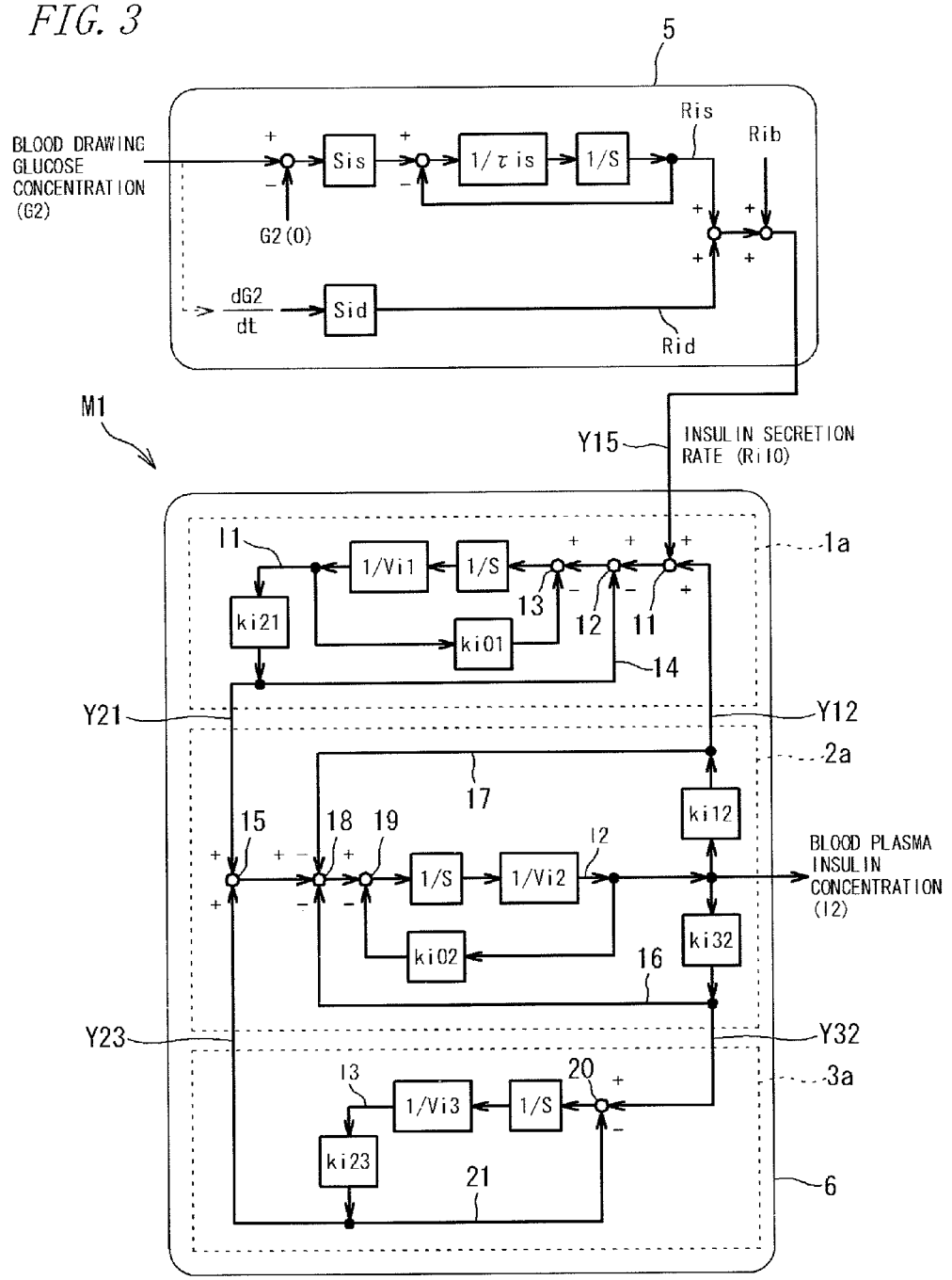
FIG. 3 is a block diagram of an insulin kinetic unit.
Figure 4:
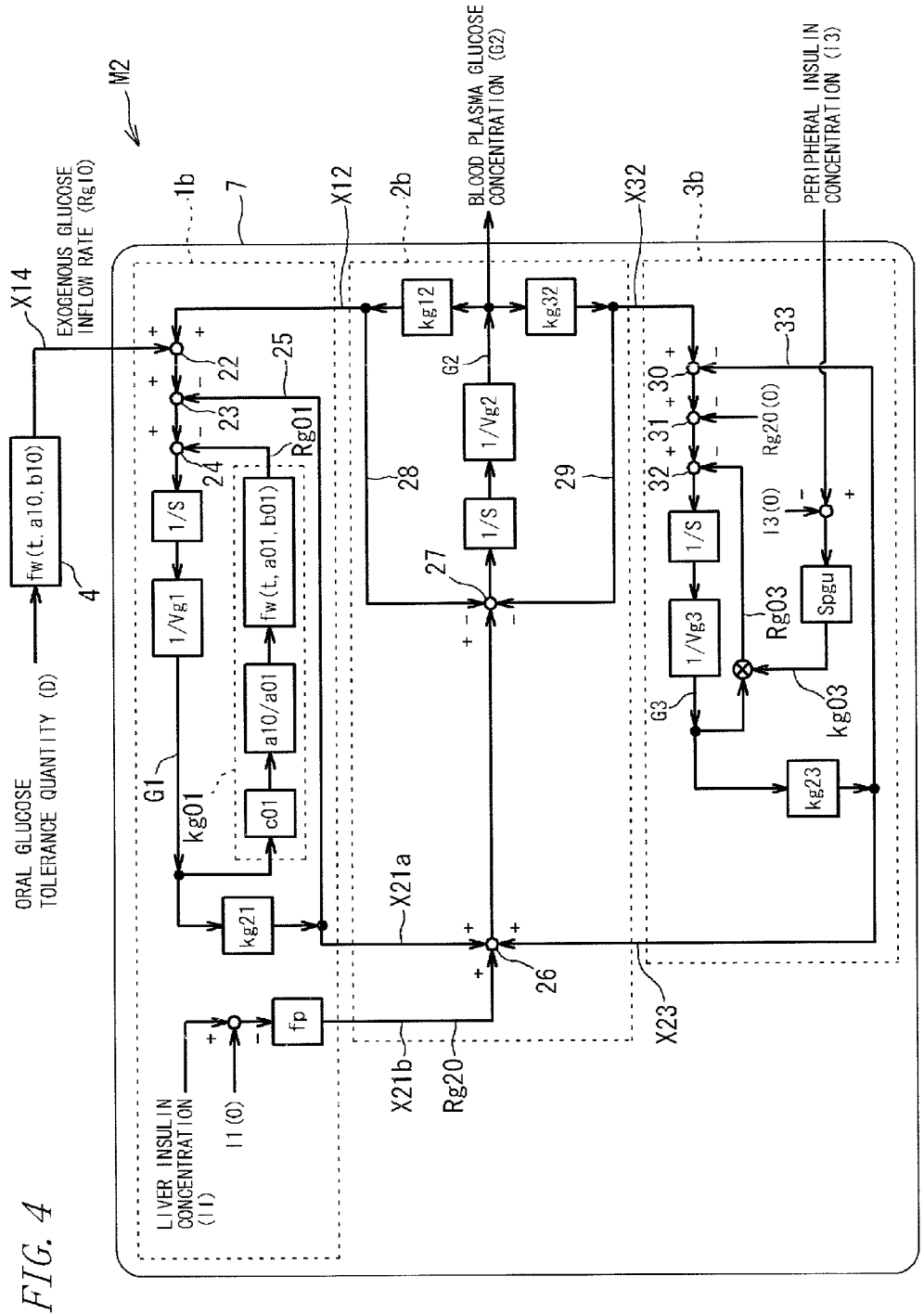
FIG. 4 is a block diagram of a glucose kinetic unit.

FIGS. 3 and 4 show an insulin kinetic unit M1 and a glucose kinetic unit M2 in further detail.

[Insulin Kinetic Unit]

As shown in FIG. 3, the insulin kinetic unit M1 includes a pancreas block 5 and an insulin kinetic block 6. The insulin kinetic block 6 is composed of a liver insulin kinetic block 1a associated with insulin in the liver block 1, a blood plasma insulin kinetic block 2a associated with insulin in the blood plasma block 2, and a peripheral insulin kinetic block 3a associated with insulin in the peripheral block 3.

Respective values used in the insulin kinetic unit M1 are shown in following Tables 1 and 2.

TABLE 1

| | | | Insulin kinetic unit | |
| --- | --- | --- | --- | --- |
| | Variable name | Unit | Description | Input source |
| Input | G2_ref(t) (=G2(t)) | mg/dl | Blood drawing glucose concentration (=blood plasma glucose concentration) | Actual measurement |
| | I2_ref(0) (=I2(0)) | µU/ml | Fasting blood drawing insulin concentration (=fasting blood plasma insulin concentration) | Actual measurement |
| | Variable name | Unit | Description | Output destination |
| Output | I2(t) | µU/ml | Blood plasma insulin concentration | Comparison with actual measurement |
| | Variable name | Unit | Description | |
| Subject to be compared | I2_ref(t) | µU/ml | Blood drawing insulin concentration | |

TABLE 2

| | Variable name | Unit | Description | |
| --- | --- | --- | --- | --- |
| Internal variable | Ri10(t) | µU/kg/min | Insulin secretion rate from pancreas to liver | |
| | Ris(t) | µU/kg/min | Insulin secretion rate depending on glucose concentration | |
| | Rid(t) | µU/kg/min | Insulin secretion rate depending on temporal variation of glucose concentration | |
| | I1(t) | µU/ml | Liver insulin concentration (interstitial fluid unit) | |
| | I2(t) | µU/ml | Blood plasma insulin concentration | |
| | I3(t) | µU/ml | Peripheral insulin concentration (interstitial fluid unit) | |
| | Name | Unit | Description | Fixed/Setup/Variable |
| Parameter | Rib | µU/kg/min | Fasting insulin production rate | Setup |
| | Sis | (dl/mg) (µU/kg/min) | Insulin secretion sensitivity depending on glucose concentration | Variable |
| | Sid | (dl/mg) (µU/kg) | Insulin secretion sensitivity depending on temporal variation of glucose concentration | Variable |

TABLE 2-continued

| | | | |
|---|---|---|---|
| τis | min | Responsivity of insulin secretion depending on glucose concentration | Variable |
| ki21 | ml/kg/min | Insulin transition rate from liver to blood plasma | Setup |
| ki12 | ml/kg/min | Insulin transition rate from blood plasma to liver | Fixed |
| ki32 | ml/kg/min | Insulin transition rate from blood plasma to periphery | Fixed |
| ki23 | ml/kg/min | Insulin transition rate from periphery to blood plasma | Setup |
| ki01 | ml/kg/min | Liver insulin disappearance rate | Fixed |
| ki02 | ml/kg/min | Blood plasma insulin disappearance rate | Fixed |
| Vi1 | ml/kg | Liver distribution capacity volume of insulin | Fixed |
| Vi2 | ml/kg | Blood plasma distribution capacity volume of insulin | Fixed |
| Vi3 | ml/kg | Peripheral distribution capacity volume of insulin | Fixed |

Among parameters of Table 2, a fixed value of a fixed parameter is set up, for example, as follows.
Vi1=88
Vi2=45
Vi3=95
ki12=12.1
ki32=1.9
ki01=16.3
ki02=5.6

Among parameters of Table 2, a setup parameter is set up based on a setup formula, for example, as follows.

$$Rib=(ki01+ki02)*I2(0)$$

$$ki23=ki32$$

$$ki21=ki12+ki32+ki02-ki23$$

Among parameters of Table 2, a variable parameter is a parameter in which a value is adjusted (searched) for generating the biological model M inherent to an individual patient at time of generation of the biological model M (insulin kinetic unit M1). A search range of respective variable parameters is, for example, as follows.
Sis: Minimum value 0 to maximum value 500
Sid: Minimum value 0 to maximum value 6000
τis: Minimum value 1 to maximum value 240

Among internal variables of Table 2, initial values of Ris, I1, and I3 are as follows.
Ris(0)=0
I1(0)=I2(0)
I3(0)=I2(0)

[Detailed Description of Computation of Pancreas Block]

A computing equation performed in the pancreas block 5 is described below (Formula 1). An insulin secretion rate Ri10 is calculated from the blood sampling glucose concentration G2. The following formula is corresponding to a block diagram in the pancreas block 5 of FIG. 3.

$$R_{i10}(t)=R_{is}(t)+R_{id}(t)+R_{ib},\ R_{i10}(t)\geq 0,\ \text{all }t \quad \text{[Formula 1]}$$

In the above-described formula, Ris and Rid other than Rib being a setup parameter is computed as follows (Formula 2).

$$\dot{R}_{is}(t)= \begin{cases} -\frac{1}{\tau_{is}}\{R_{is}(t)-S_{is}[G_2(t)-G_2(0)]\} & \text{if } G_2(t)-G_2(0)>0 \\ -\frac{1}{\tau_{is}}R_{is}(t) & \text{if } G_2(t)-G_2(0)\leq 0 \end{cases} \quad \text{[Formula 2]}$$

$$R_{id}(t)= \begin{cases} S_{id}\dot{G}_2(t) & \text{if } \dot{G}_2(t)>0 \\ 0 & \text{if } \dot{G}_2(t)\leq 0 \end{cases}$$

Ris in the above-described formula is an insulin secretion rate depending on the glucose concentration G2. It is calculated based on the insulin secretion sensitivity Sis depending on a glucose concentration and the insulin secretion responsivity τis depending on the glucose concentration. Rid in the above-described formula is an insulin secretion rate depending on "temporal variation" of the glucose concentration G2. It is calculated based on a derivative value (dG2/dt) of the glucose concentration and the insulin secretion sensitivity Sid depending on the temporal variation of the glucose concentration. Sis, τis, and Sid which are parameters to determine the above-described insulin secretion rates Ris(t) and Rid(t) are variable parameters for searching a value corresponding to an individual patient at the time of biological model generation. Therefore, it is possible to obtain an insulin secretion rate corresponding to an individual patient.

Further, according to the present embodiment, with respect to the insulin secretion rate, not only Ris(t) calculated by "glucose concentration G2(t)" but also Rid(t) calculated in response to "glucose concentration G2(t)" is calculated independently from Ris(t). Therefore, it is possible to analyze an insulin secretion function at early stage immediately after the glucose tolerance by utilizing Rid(t).

Thus the pancreas block 5 accepts the blood sampling glucose concentration G2(t) being the result of OGTT as an external input and outputs the insulin secretion rate Ri10 which is obtained as described above to the insulin kinetic block 6 (liver insulin kinetic block 1a).

The computing equation which is performed by respective blocks 1a, 1b, and 1c of the insulin kinetic block 6 is described below (Formula 3). The following formulas are corresponding to block diagram of respective blocks 1a, 1b, and 1c.

Liver insulin kinetic block: [Formula 3]

$$V_{i1}\frac{dI_1(t)}{dt} = -(k_{i21}+k_{i01})I_1(t)+k_{i12}I_2(t)+R_{i10}(t)$$

Blood plasma insulin kinetic block:

$$V_{i2}\frac{dI_2(t)}{dt} = -(k_{i12}+k_{i32}+k_{i02})I_2(t)+k_{i21}I_1(t)+k_{i23}I_3(t)$$

Peripheral insulin kinetic block:

$$V_{i3}\frac{dI_3(t)}{dt} = -k_{i23}I_3(t)+k_{i32}I_2(t)$$

As shown above, the respective insulin kinetic blocks 1a, 1b, and 1c calculate insulin concentrations I1(t), I2(t), and I3(t) in the respective blocks.

[Detailed Computation in Liver Insulin Kinetic Block]

In the liver insulin kinetic block 1a, there are Y15 and Y12 as insulin inflow. Sum of these is a total inflow quantity. A computing unit 11 is provided for obtaining a sum of Y15 and Y12. Further, in the liver insulin kinetic block 1a, there is Y21 as insulin outflow. For obtaining the insulin concentration (cumulative quantity) in the liver insulin kinetic block 1a, it is required to subtract an insulin outflow quantity Y21 from a total insulin inflow quantity. For performing this subtraction, a loupe 14 is provide for feeding back the insulin outflow Y21 to inflow side, and a computing unit 12 is provided for subtracting the outflow quantity Y21 from the total inflow quantity (Y15+Y12).

Further, because insulin disappears to some extent in the liver, it is required to subtract a portion of disappearance from (Y15+Y12−Y21) for accurately obtaining an insulin concentration (cumulative quantity) in the liver insulin kinetic block 1a. This subtraction is performed by a computing unit 13. The computing unit 13 subtracts a portion of disappearance which is obtained based on a liver insulin concentration I1(t) and a liver insulin disappearance rate ki01.

Output of the computing unit 13 reflects inflow and outflow of insulin and disappearance of the liver insulin in the liver insulin kinetic block 1a and indicates a value of insulin balance (insulin rate). In the liver insulin kinetic block 1a, this value is integral-operated (1/S) for obtaining the liver insulin cumulative quantity. Further the liver insulin concentration I1(t) is calculated by multiplying the liver insulin cumulative quantity by an inverse number of a liver distribution capacity volume Vi1 of insulin.

Further, in the liver insulin kinetic block 1a, thus calculated liver insulin concentration I1(t) is multiplied by the insulin transition rate ki21 for obtaining the insulin inflow rate (Y21) into the blood plasma insulin kinetic block 2a. Thus insulin inflow rate (Y21) is outputted to the blood plasma insulin kinetic block 2a.

[Detailed Computation in Blood Plasma Insulin Kinetic Block]

In the blood plasma insulin kinetic block 2a, there are Y21 and Y23 as insulin inflow. Sum of these is a total inflow quantity. A computing unit 15 is provided for obtaining the sum of Y21 and Y23. Further, in the blood plasma insulin kinetic block 2a, there are Y12 and Y32 as insulin outflow. It is required to subtract a total insulin outflow quantity (Y12+Y32) from the total insulin inflow quantity (Y21+Y23) for obtaining the insulin concentration (cumulative quantity) in the blood plasma insulin kinetic block 2a. For performing this subtraction, loupes 16 and 17 are provided for feeding back the insulin outflow to inflow side, and a computing unit 18 is provided for subtracting the total outflow quantity (Y12+Y32) from the total inflow quantity (Y21+Y23).

Further, because insulin disappears to some extent in the blood plasma, it is required to subtract a portion of disappearance from ((Y21+Y23)−(Y12+Y32)) for accurately obtaining the insulin concentration (cumulative quantity) in the blood plasma insulin kinetic block 2a. This subtraction is performed by a computing unit 19. The computing unit 19 subtracts a portion of disappearance which is obtained based on a blood plasma insulin concentration I2(t) and a blood plasma insulin disappearance rate ki02.

Output of the computing unit 19 reflects inflow and outflow of insulin and disappearance of the liver insulin in the blood plasma insulin kinetic block 2a and indicates a value of insulin balance (insulin rate). The blood plasma insulin cumulative quantity is calculated by integrally operating (1/S) this value. Further the blood plasma insulin concentration I2(t) is calculated by multiplying the blood plasma insulin cumulative quantity by an inverse number of a blood plasma distribution capacity volume Vi2 of insulin.

Further, in the blood plasma insulin kinetic block 2a, the insulin inflow rate (Y12) into the liver insulin kinetic block 1a is obtained by multiplying the calculated blood plasma insulin concentration I2(t) by the insulin transition rate ki12, and the insulin inflow rate is outputted to the liver insulin kinetic block 1a. Further, the insulin inflow rate (Y32) into the peripheral insulin kinetic block 3a is obtained by multiplying the calculated blood plasma insulin concentration I2(t) by the insulin transition rate ki32, and the insulin inflow rate is outputted to the peripheral insulin kinetic block 3a.

[Detailed Computation in Peripheral Insulin Kinetic Block]

In the peripheral insulin kinetic block 3a, there are Y32 as insulin inflow and Y23 as insulin outflow. Therefore, it is required to subtract the insulin outflow quantity Y23 from the insulin inflow quantity Y32 for obtaining the insulin concentration (cumulative quantity) in the peripheral insulin kinetic block 3a. For performing this subtraction, a loupe 21 is provided for feeding back the insulin outflow Y23 to inflow side, and a computing unit 21 is provided for subtracting the outflow quantity Y23 from the inflow quantity Y32.

Output of the computing unit 21 reflects inflow and outflow of insulin in the peripheral insulin kinetic block 3a and indicates a value of insulin balance (insulin inflow rate). In the peripheral insulin kinetic block 3a, the peripheral insulin cumulative quantity is obtained by integrally operating (1/S) this value. Further the peripheral insulin concentration I3(t) is calculated by multiplying the peripheral insulin cumulative quantity by an inverse number of a peripheral distribution capacity volume Vi3 of insulin.

Further, in the peripheral insulin kinetic block 3a, the insulin inflow rate (Y23) into the blood plasma insulin kinetic block 2a is obtained by multiplying the calculated peripheral insulin concentration I3(t) by the insulin transition rate ki23, and the insulin inflow rate is outputted to the blood plasma insulin kinetic block 2a.

[Glucose Kinetic Unit]

As shown in FIG. 4, the glucose kinetic unit M2 includes an intestine block 5 and a glucose kinetic block 7. The glucose kinetic block 7 is composed of a liver glucose kinetic block 1b associated with glucose in the liver block 1, a blood plasma glucose kinetic block 2b associated with glucose in the blood plasma block 2, and a peripheral glucose kinetic block 3b associated with glucose in the peripheral block 3.

Respective values used in the glucose kinetic unit M2 are shown in the following Tables 3 to 6.

TABLE 3

| Block name | Variable name | Unit | Description | Input source |
|---|---|---|---|---|
| Input | I1(t) | µU/ml | Liver insulin concentration | Calculation with insulin kinetic unit |
| | I3(t) | µU/ml | Peripheral insulin concentration | Calculation with insulin kinetic unit |
| | G2(0) | mg/dl | Fasting blood drawing glucose concentration | Actual measurement |
| | D | mg/kg | Oral glucose tolerance quantity | Actual measurement |
| | Variable name | Unit | Description | Output destination |
| Output | G2(t) | mg/dl | Blood plasma glucose concentration | Comparison with actual measurement |
| | Variable name | Unit | Description | |
| Subject to be compared | G2_ref(t) | mg/dl | Blood drawing glucose concentration | |

TABLE 4

| | Variable name | Unit | Description |
|---|---|---|---|
| Internal variable | Rg10(t) | mg/kg/min | Exogenous glucose inflow rate into liver |
| | Rg20(t) | mg/kg/min | Liver glucose production rate |
| | Rg01(t) | mg/kg/min | Liver glucose uptake rate |
| | Rg03(t) | mg/kg/min | Periphery uptake rate variation to basis |
| | G1(t) | mg/dl | Liver glucose concentration |
| | G2(t) | mg/dl | Blood plasma glucose concentration |
| | G3(t) | mg/dl | Peripheral glucose concentration |
| | I1(t) | µU/ml | Liver insulin concentration |
| | I2(t) | µU/ml | Blood plasma insulin concentration |
| | I3(t) | µU/ml | Peripheral insulin concentration |
| | kg01(t) | l/min | Liver glucose uptake rate |
| | kg03(t) | l/min | Peripheral glucose uptake rate variation to basis |

TABLE 5

| | Name | Unit | Description | Fixed/Setup/Variable |
|---|---|---|---|---|
| Parameter | Rg20(0) | mg/kg/min | Fasting liver glucose production rate | Setup |
| | a10 | l/min | Weibull function shape parameter associated with Rg10 | Setup |
| | a01 | l/min | Weibull function shape parameter associated with Rg01 | Variable |
| | aoff | l/min | Offset value associated with a10 | Fixed |
| | b10 | *** | Weibull function scale parameter associated with Rg10 | Fixed |
| | b01 | *** | Weibull function scale parameter associated with Rg01 | Fixed |
| | c01 | *** | Parameter associated with Rg01 | Fixed |
| | Pup | dl/kg/min | Parameter associated with liver glucose production | Fixed |
| | Poff | mg/kg/min | Offset value associated with liver glucose production | Fixed |
| | Pexp | *** | Parameter associated with liver glucose production | Fixed |
| | I50 | µU/ml | Insulin increase quantity to basic secretion required for inhibiting liver glucose production by 50% | Setup |
| | P50 | (dl/mg)(µU/ml) | Dependency of I50 on fasting blood glucose level | Fixed |
| | Spgu | (ml*dl)/(µU*kg*min) | Peripheral glucose uptake sensitivity | Variable |
| | kg21 | dl/kg/min | Glucose transition ratio from liver to blood plasma | Setup |
| | kg12 | dl/kg/min | Glucose transition ratio from blood plasma to liver | Fixed |
| | kg23 | dl/kg/min | Glucose transition ratio from periphery to blood plasma | Setup |

TABLE 5-continued

| Name | Unit | Description | Fixed/Setup/Variable |
|---|---|---|---|
| kg32 | dl/kg/min | Glucose transition ratio from blood plasma to periphery | Fixed |
| Vg1 | dl/kg | Liver distribution capacity volume of glucose | Fixed |
| Vg2 | dl/kg | Blood plasma distribution capacity volume of glucose | Fixed |
| Vg3 | dl/kg | Peripheral distribution capacity volume of glucose | Fixed |

TABLE 6

| | Variable name | Unit | Description |
|---|---|---|---|
| Others | fw(t, a, b) | l/min | Weibull function associated with Rg10 and Rg01 |
| | fp(I, I50, p) | *** | Function associated with liver glucose production inhibition |

Among parameters of Table 5, a fixed value of a fixed parameter is set up, for example, as follows.
Vg1=0.88
Vg2=0.45
Vg3=0.95
kg12=0.464
kg32=0.131
Pup=0.008
Poff=1.9
Pexp=1.38
P50=0.2
aoff=160
b10=1.4
c01=1.5

Among parameters of Table 5, a setup parameter is set up based on a setup formula. The setup formula is, for example, as the following formula.

$$kg23 = kg32 - (Rg20(0)/G2(0))$$

$$kg21 = kg12$$

$$a10 = aoff - a01$$

$$b01 = b10$$

$$I50 = p50 * G2(0)$$

Among parameters of Table 5, a variable parameter is a parameter in which a value is adjusted (searched) for generating the biological model M inherent to an individual patient at the time of generation of the biological model M (glucose kinetic unit M2). A search range of respective variable parameters is, for example, as follows.

a01: Minimum value 10 to maximum value 150
Spgu: Minimum value 0 to maximum value 0.16

Among internal variables of Table 4, initial values of Rg20, G1, and G3 are as follows.

$$Rg20(0) = (Pup \times G2(0) + poff)$$

$$G1(0) = G2(0)$$

$$G3(0) = G2(0)$$

Computing equations performed in the intestine block 4 and respective blocks 1b, 2b, and 3b of the glucose kinetic block 7 are described below (Formulas 4 to 11). The following formulas are corresponding to a block diagram in FIG. 4.

Liver glucose kinetic block: [Formula 4]

$$V_{g1}\frac{dG_1(t)}{dt} = -(k_{g21} + k_{g01}(t))G_1(t) + k_{g12}G_2(t) + R_{g10}(t)$$

Blood plasma glucose kinetic block:

$$V_{g2}\frac{dG_2(t)}{dt} = -(k_{g12} + k_{g32})G_2(t) + k_{g21}G_1(t) + k_{g23}G_3(t) + R_{g20}(t)$$

Peripheral glucose kinetic block:

$$V_{g3}\frac{dG_3(t)}{dt} = -(k_{g23} + k_{g03}(t))G_3(t) + k_{g32}G_2(t) - R_{g20}(0)$$

As shown in the above-described formulas, the respective glucose kinetic blocks 1b, 2b, and 3b calculate glucose concentrations G1(t), G2(t), and G3(t) in the respective blocks.

Weibull function: $f_w(t, a, b) = \frac{bt^{b-1}}{a^b}\exp\left(-\frac{t^b}{a^b}\right)$ [Formula 5]

Function associated with the liver glucose production inhibition $f_p(I, I_{50}, p) = \frac{I_{50}^p}{I_{50}^p + I^p}$ [Formula 6]

Exogenous glucose inflow rate into the liver: [Formula 7]

$$R_{g10}(t) = D * f_w(t, a_{10}, b_{10})$$

Liver glucose production rate: [Formula 8]

$$R_{g20}(t) = \begin{cases} (p_{up}G_1(0) + p_{off}) * \\ f_p(I_1(t) - I_1(0), I_{50}, p_{exp}) & \text{if } I_1(t) - I_1(0) > 0 \\ (p_{up}G_1(0) + p_{off}) & \text{if } I_1(t) - I_1(0) \le 0 \end{cases}$$

Liver glucose uptake rate: [Formula 9]

$$k_{g01}(t) = \begin{cases} c_{01}\frac{a_{10}}{a_{01}} * f_w(t, a_{01}, b_{01}) & \text{if } G_1(t) - G_1(0) > 0 \\ 0 & \text{if } G_1(t) - G_1(0) \le 0 \end{cases}$$

Variation of peripheral glucose uptake rate to basis:

$$k_{g03}(t) = \begin{cases} S_{pgu}(I_3(t) - I_3(0)) & \text{if } I_3(t) - I_3(0) > 0 \\ 0 & \text{if } I_3(t) - I_3(0) \le 0 \end{cases}$$

Liver glucose uptake rate: $R_{g01}(t) = k_{g01}G_1$ [Formula 10]

Peripheral glucose uptake rate: [Formula 11]

$$PGU(t) = R_{g03}(t) + R_{g20}(0) = k_{g03}G_3 + R_{g20}(0)$$

{Detailed Computation in Intestine Block}

The intestine block 4 calculates the exogenous glucose inflow rate Rg10(X14) into the liver glucose kinetic block 1b. The exogenous glucose inflow rate Rg10 into the liver glucose kinetic block 1b is calculated by multiplying an oral glucose tolerance quantity D in OGTT by a Weibull function, as shown above (Formula 7).

The Weibull function is a function as shown above (Formula 5) which describes probability distribution proposed for statistically describing strength of the object. In the above (Formula 5), a refers to shape parameter and b refers to scale parameter. In a parameter range used in the present embodiment, the smaller shape parameter a has the larger maximum value, and the smaller scale parameter b takes the shorter time to reach the maximum value.

Among the Weibull function parameters shown above (Formula 7), the shape parameter a10 is a value which is to be set up based on the parameter a01 and the offset value a0ff, and the parameter a01 is a variable parameter in which a value is searched in response to an individual patient at the time of generation of biological model. Therefore, in the parameter a10, a value is adjusted in response to the individual patient. Accordingly, the exogenous glucose inflow rate Rg10 (X14) into the liver glucose kinetic block 1b is adjusted in response to the individual patent. In other words, the intestine block 4 functions as a control unit for controlling the exogenous glucose inflow rate into the liver glucose kinetic block 1b.

Thus, according to the present embodiment, since the intestine block 4 which functions as the control unit for controlling the exogenous glucose inflow rate is provided, it is possible that the present system 100 provides information useful to a pathological condition analysis of the patient who requires care to glucose absorption from the intestine.

In other words, it is possible to objectively and accurately catch variation of patient's conditions due to α-glucosidase inhibitor. As a result, it is possible that the present system 100 provides useful information for appropriately providing judgment and treatment depending on temporal states.

Here, carbohydrate taken in at meals is decomposed into polysaccharide, oligosaccharide, and disaccharide, and further decomposed into monosaccharide due to α-glucosidase in the intestine, and absorbed in the small intestine. The α-glucosidase inhibitor is a glucose absorption inhibitor which lowers glucose absorption from the intestine by inhibiting decomposition of the disaccharide.

In some cases, there is a big difference in rate of glucose absorption from the intestine between a patient who takes the α-glucosidase inhibitor and a patient who does not take it. In the system according to the present embodiment, the intestine block 4 is provided and a parameter a10 is adjusted (searched) for adapting this intestine block 4 to the individual patient. Therefore, an exogenous glucose inflow rate Rg10 (X14) is appropriately represented for every individual patient.

[Detailed Computation in Liver Glucose Kinetic Block]

In the liver glucose kinetic block 1b, there are X14 and X12 as glucose inflow. Sum of these is a total inflow quantity. A computing unit 22 is provided for obtaining the sum of X14 and X12. Further, in the liver glucose kinetic block 1b, there is X21a as glucose outflow. It is required to subtract a glucose outflow quantity X21a from a total glucose inflow quantity (X14+X12) for obtaining the glucose concentration (cumulative quantity) in the liver glucose kinetic block 1b. For performing this subtraction, a loupe 25 is provided for feeding back the glucose outflow X21a to inflow side. A computing unit 23 is provided for subtracting the glucose outflow quantity X21a from the total glucose inflow quantity (X14+X12).

Further, because a glucose is taken up in the liver, it is required to subtract glucose being a portion of disappearance from the interstitial fluid of the liver due to the liver glucose uptake from (X14+X12−X21a) for accurately obtaining the glucose concentration (cumulative quantity) in the liver glucose kinetic block 1b. This subtraction is performed by a computing unit 24.

The liver glucose uptake rate Rg01 in the liver glucose kinetic block 1b is calculated by the above (Formula 10). The liver glucose uptake rate Rg01 is calculated based on the liver glucose concentration G1(t) and the liver glucose uptake ratio kg01 in the liver glucose kinetic block 1b. Here, a formula for obtaining the liver glucose uptake rate kg01 includes a parameter a01 as shown in the above (Formula 9). This parameter a01 is a variable parameter for searching a value corresponding to the individual patient at the time of generation of biological model. Therefore, the liver glucose uptake ratio kg01 corresponding to the individual patient is obtained, and further the liver glucose uptake rate Rg01 corresponding to the individual patient is obtained. Further, a relational expression that the parameter a01 and the parameter a10 mutually depend on each other is used. This is purposed to express a relation that the lower the liver glucose uptake function is, the more the glucose release from the liver increases.

Output of the computing unit 24 reflects inflow and outflow of glucose and liver glucose uptake in the liver glucose kinetic block 1b and indicates a value of glucose balance (glucose rate). In the liver glucose kinetic block 1b, the liver glucose cumulative quantity is obtained by integrally operating (1/S) this value. Further the liver glucose concentration G1(t) is calculated by multiplying the liver glucose cumulative quantity by an inverse number of a liver distribution capacity volume Vg1 of glucose.

Further, in the liver glucose kinetic block 1b, the first glucose inflow rate (X21a) into the blood plasma glucose kinetic block 2b is obtained by multiplying the calculated liver glucose concentration G1(t) by the glucose transition ratio kg21. Thus first glucose inflow rate (X21) is outputted to the blood plasma glucose kinetic block 2b.

Further, the liver glucose kinetic block 1b calculates a liver glucose production rate Rg20 based on the liver insulin concentration I1 calculated by the liver insulin kinetic block 1a. The liver glucose production rate Rg20 is calculated based on the above (Formula 8). In Formula 8 for calculating the liver glucose production rate Rg20, a function fp associated with liver glucose production inhibition indicated in Formula 6 is included. Thus calculated liver glucose production rate Rg20 is outputted to the blood plasma glucose kinetic block 2b as the second glucose inflow rate (X21b) into the blood plasma glucose kinetic block 2b. Thus, two glucose inflow rates X21a and X21b are provided from the liver glucose kinetic block 1b to the blood plasma glucose kinetic block 2b.

[Detailed Computation in Blood Plasma Glucose Kinetic Block]

In the blood plasma glucose kinetic block 2b, there are X21a, X21b, and X23 as glucose inflow. Sum of these is a total inflow quantity. A computing unit 26 is provided for obtaining the sum of X21a, X21b, and X23. Further, in the blood plasma glucose kinetic block 2b, there are X12 and X32 as glucose outflow. It is required to subtract a total glucose outflow quantity (X12+X32) from a total glucose inflow quantity (X21a+X21b+X23) for obtaining the glucose concentration (cumulative quantity) in the blood plasma glucose kinetic block 2b. For performing this subtraction, loupes 28 and 29 are provided for feeding back the glucose outflow to inflow side. A computing unit 27 is provided for subtracting the total outflow quantity (X12+X32) from the total inflow quantity (X21a+X21b+X23).

Output of the computing unit 27 reflects inflow and outflow of glucose in the blood plasma glucose kinetic block 2b and indicates a value of glucose balance (glucose rate). The blood plasma glucose cumulative quantity is obtained by integrally operating (1/S) this value. Further the blood plasma glucose concentration G2(t) is calculated by multiplying the blood plasma glucose cumulative quantity by an inverse number of a blood plasma distribution capacity volume Vg2 of glucose.

Further, in the blood plasma glucose kinetic block 2b, a glucose inflow rate (X12) into the liver glucose kinetic block 1b is obtained by multiplying the calculated blood plasma glucose concentration G2(t) by a glucose transition ratio kg12. Thus glucose inflow rate is outputted to the liver glucose kinetic block 1b. Further, a glucose inflow rate (X32) into the peripheral glucose kinetic block 3b is obtained by multiplying the calculated blood plasma glucose concentration G2(t) by a glucose transition ratio kg32. Thus glucose inflow rate is outputted to the peripheral glucose kinetic block 3b.

[Detailed Computation in Peripheral Glucose Kinetic Block]

In the peripheral glucose kinetic block 3b, there are X32 as glucose inflow and X23 as glucose outflow. Therefore, for obtaining a glucose concentration (cumulative quantity) in the peripheral glucose kinetic block 3b, it is required to subtract the glucose outflow quantity X23 from the glucose inflow quantity X32. For performing this subtraction, a loupe 33 is provided for feeding back the glucose outflow X23 to inflow side. A computing unit 30 is provided for subtracting the outflow quantity X23 from the inflow quantity X32.

Further, because a glucose is taken up in the periphery, it is required to subtract glucose being a portion of disappearance from the interstitial fluid of the peripheral tissue due to the peripheral glucose uptake from (X32−X23) for accurately obtaining the glucose concentration (cumulative quantity) in the peripheral glucose kinetic block 3b. This subtraction is performed by computing units 31 and 32.

The peripheral glucose uptake rate PGU(t) in the peripheral glucose kinetic block 3b is calculated by the above (Formula 11). The peripheral glucose uptake rate PGU(t) is calculated as a sum of an initial value Rg20(0) of the liver glucose production rate and variation Rg03 of the peripheral glucose uptake ratio to a basis. As shown in the above (Formula 11), the variation Rg03 of the peripheral glucose uptake rate to a basis is calculated by multiplying the variation kg03(t) of the peripheral glucose uptake ratio to a basis by the peripheral glucose concentration G3(t).

As shown in the above (Formula 9), the variation kg03(t) of the peripheral glucose uptake ratio to a basis is calculated by multiplying the peripheral insulin concentration I3(t) which is calculated by the peripheral insulin kinetic block 3a, by a peripheral glucose uptake sensitivity Spgu. This peripheral glucose uptake sensitivity Spgu is a variable parameter for searching a value corresponding to the individual patient at the time of generation of biological model. Therefore, the peripheral glucose uptake sensitivity Spgu corresponding to the individual patient is obtained, and further, the peripheral glucose uptake rate PGU(t) corresponding to the individual patient is obtained.

Output of the computing unit 32 performing subtraction of the peripheral glucose uptake rate reflects inflow and outflow of glucose in the peripheral glucose kinetic block 3b and peripheral glucose uptake and indicates a value of glucose balance (glucose rate).

In the peripheral glucose kinetic block 3b, the peripheral glucose cumulative quantity is obtained by integrally operating (1/S) this value. Further, the peripheral glucose concentration G3(t) is calculated by multiplying the peripheral glucose cumulative quantity by an inverse number of a peripheral distribution capacity volume Vg3 of glucose.

Further, in the peripheral glucose kinetic block 3b, a glucose inflow rate (X23) into the blood plasma glucose kinetic block 2b is obtained by multiplying the calculated peripheral glucose concentration G3(t) by a glucose transition ratio kg23. Thus glucose inflow rate is outputted to the blood plasma glucose kinetic block 2b.

[Overall Configuration of System]

Figure 5:
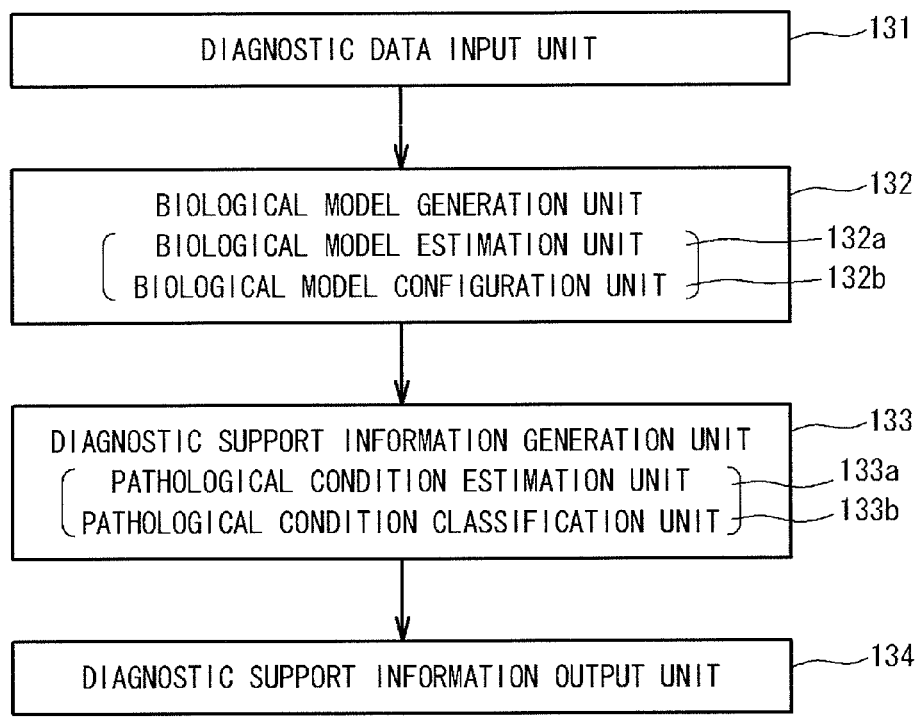
FIG. 5 is a function block diagram of a diagnostic support system for diabetes.

FIG. 5 shows an overall configuration of the present system 100. The system 100 has a diagnostic data input unit 131, a biological model generation unit 132, a diagnostic support information generation unit 133, and a diagnostic support information output unit 134. The biological model generation unit 132 includes a biological model estimation unit 132a and a biological model configuration unit 132b. The diagnostic support information generation unit 133 includes a pathological condition estimation unit 132a and a pathological condition classification unit 132b.

The diagnostic data input unit 131 is provided for inputting in the present system 100 a numerical value (laboratory value) such as a blood drawing glucose concentration and a blood drawing insulin concentration which are actually measured by OGTT and a meal tolerance test (MT), finding information obtained through doctor's inquires, various information which are already inputted in database and others, and others. Inputted information is stored in a nonvolatile memory device such as a hard disk 110d so that the inputted information can be used in the biological model generation unit 132 and others. As diagnostic data inputted by the input unit 131, there are an oral glucose tolerance quantity D besides a blood drawing glucose concentration G2_ref and a blood drawing insulin concentration I2_ref(t). Further, as the finding information (clinical findings) to be inputted, there are a state of obesity or thinness, a state of carbohydrate intake and others.

The biological model configuration unit 132b of the biological model generation unit 132 performs the computations in the biological model M described above. It computes an insulin secretion rate Ri10(t), a liver insulin concentration I1(t), a blood plasma insulin concentration I2(t), a peripheral insulin concentration I3(t), an exogenous glucose inflow rate into the liver block 1 Rg10(t), a liver glucose concentration G1(t), a blood plasma glucose concentration G2(t), a peripheral glucose concentration G3(t), a liver glucose uptake rate Rg01(t), a liver glucose production rate Rg20(t), a peripheral glucose uptake rate PGU(t), and others according to (Formula 1) to (Formula 11) based on the inputted diagnostic data.

The biological model estimation unit 132a of the biological model generation unit 132 is provided for estimating a biological model M suitable for reproducing behavior of the biological body. It determines a variable parameter so as to match output of the biological model M to a test result (result of glucose tolerance test) of the patient which is inputted as diagnostic data.

The biological model estimation unit 132a adjusts variable parameter within a search range and causes the biological model configuration unit 132b to compute the biological model M with a candidate variable parameter value. Here, a candidate value of the variable parameter is determined by genetic algorithm. However, it may be determined by random numbers or a heretofore known optimization method. The biological model estimation unit 132a sets the candidate value of the variable parameter as the variable parameter of the biological model M and causes the biological model configuration unit 132b to compute the biological model M. Thereby, the blood plasma glucose concentration G2(t) and the blood plasma insulin concentration I2(t) which are outputted from the biological model M are compared with the blood sampling glucose concentration G2_ref(t) and the blood sampling insulin concentration I2_ref(t), respectively.

Such comparison is carried out repeatedly by changing variable parameter candidate values, and such candidate value as having a small difference between the output from the biological model and the actual measurement value is determined as a variable parameter. The biological model M having the variable parameter thus determined is capable of reproducing a pseudo-response simulating a result of the glucose tolerance test of individual patient. Therefore, the respective parameters/variables held by the biological model M as a mathematical model represent characteristics of the individual patient.

Figure 6:
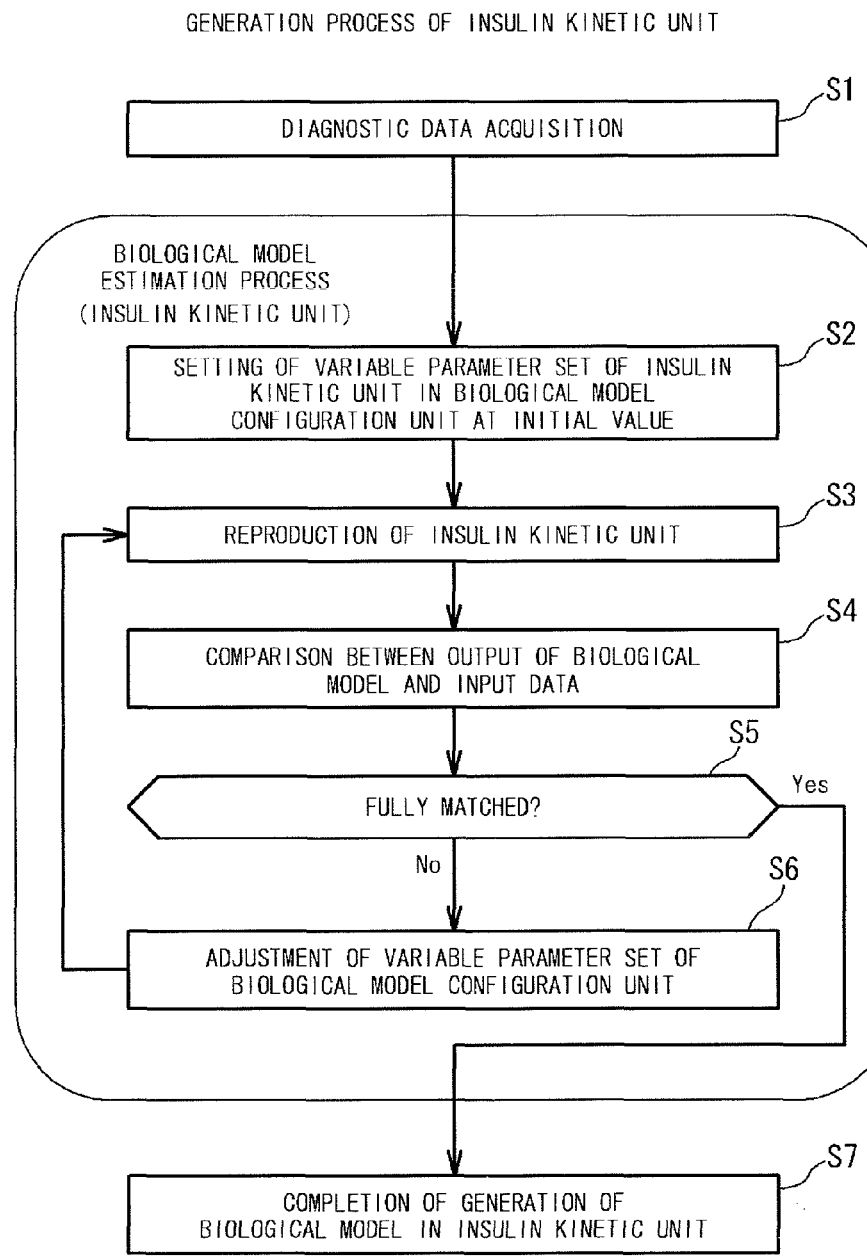
FIG. 6 is a flowchart showing an insulin kinetic unit generation process.
Figure 7:
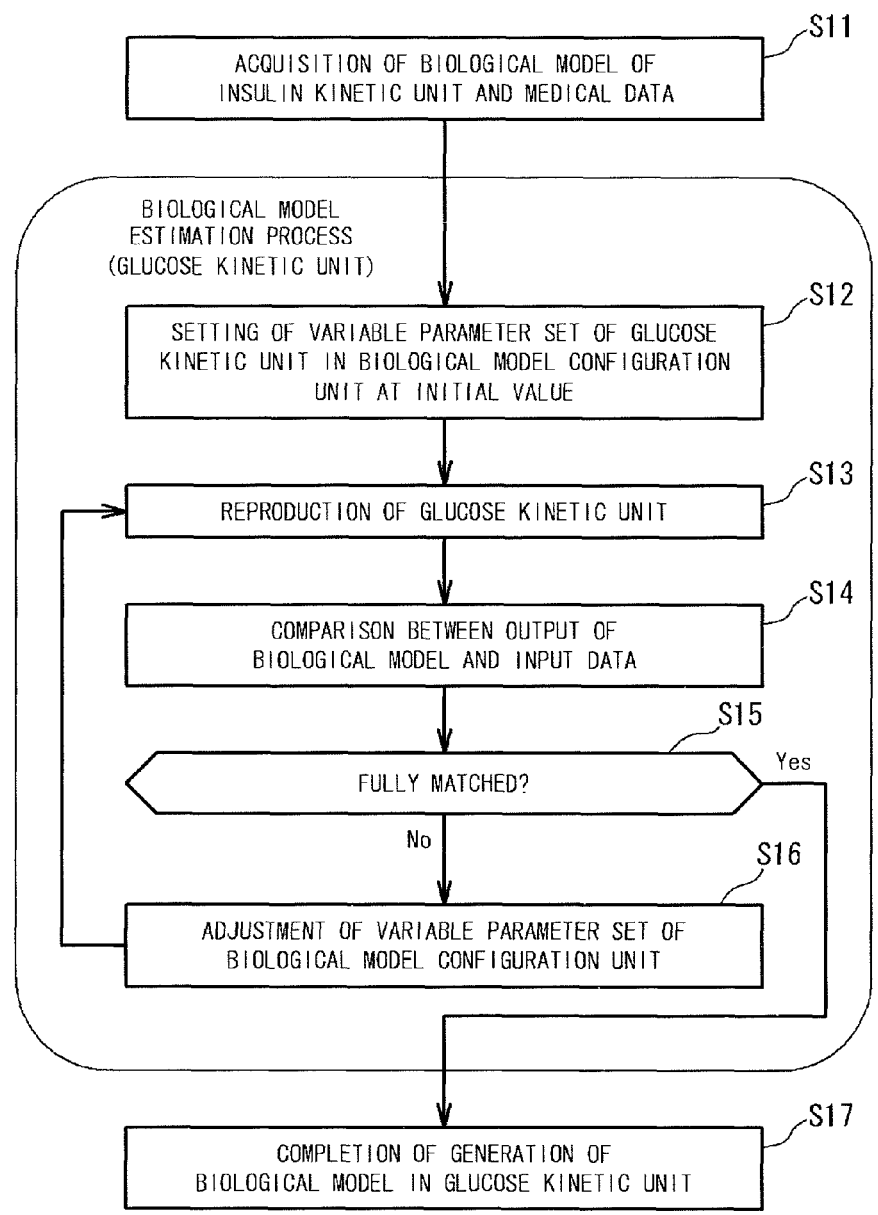
FIG. 7 is a flowchart showing a glucose kinetic unit generation process.

FIGS. 6 and 7 show processing procedures for generating the biological model M inherent to the individual patient. According to the present embodiment, an insulin kinetic unit M1 is first generated, and subsequently a glucose kinetic unit M2 is generated. A calculation here may be performed using MATLAB (manufactured by The MathWorks, Inc.) and E-Cell (software disclosed by Keio University).

As shown in FIG. 6, when the insulin kinetic unit M1 is generated, the biological model estimation unit 132a first acquires the blood sampling glucose concentration G2_ref(t) and others which are necessary as input of the insulin kinetic unit M1 among inputted diagnostic data (Step S1). Then, the biological model estimation unit 132a sets up a variable parameter set (Sis, Sid, τis) of the insulin kinetic block M1 as an appropriate initial value (Step S2).

Then, the biological model estimation unit 132a causes the biological model configuration unit 132b to compute in the insulin kinetic unit M1 based on an input value such as G2_ref (t) and reproduces the insulin kinetic unit of the patient (Step S3).

Then, the biological model estimation unit 132a compares the blood plasma insulin concentration I2(t) outputted from the insulin kinetic unit M1 with the blood sampling insulin concentration I2_ref(t) being an actual measurement value (Step S4). In a case where both are not fully matched (Step S5), respective values of the variable parameter set are adjusted (Step S6) and causes the insulin kinetic unit M1 to compute again. The variable parameter set is repeatedly adjusted. In a case where the both are fully matched, generation of the insulin kinetic unit M1 is completed (Step S7). Here, thus generated insulin kinetic unit M1 (respective values of variables/parameters thereof) is memorized in the memory device.

When the glucose kinetic unit M2 is subsequently generated, as shown in FIG. 6, the biological model estimation unit 132a acquires a value, from the memory device, which is necessary as input of the glucose kinetic unit M2, such as the liver insulin concentration I1(t) and the peripheral insulin concentration I3(t) which are calculated by the insulin kinetic unit M1. It also acquires a value which is necessary as input of the glucose kinetic unit M2, such as an oral glucose tolerance quantity D among inputted diagnostic data (Step S11).

Then, the biological model estimation unit 132a sets up a variable parameter set (a01, Spgu) of the glucose kinetic block M2 as an appropriate initial value (Step S12).

Then, the biological model estimation unit 132a causes the biological model configuration unit 132b to compute in the glucose kinetic unit M2 based on the input value such as glucose tolerance quantity D and reproduces the glucose kinetic unit of patient (Step S13).

Then, the biological model estimation unit 132a compares the blood plasma glucose concentration G2(t) outputted from the glucose kinetic unit M2 with the blood sampling glucose concentration G2_ref(t) being an actual measurement value (Step S14). In a case where both are not fully matched (Step S5), respective values of the variable parameter set are adjusted (Step S16) and causes the glucose kinetic unit M2 to compute again. The variable parameter set is repeatedly adjusted. In a case where the both are fully matched, generation of the glucose kinetic unit M2 is completed (Step S17). Here, thus generated glucose kinetic unit M2 (respective values of variables/parameters thereof) is memorized in the memory device.

Figure 8:
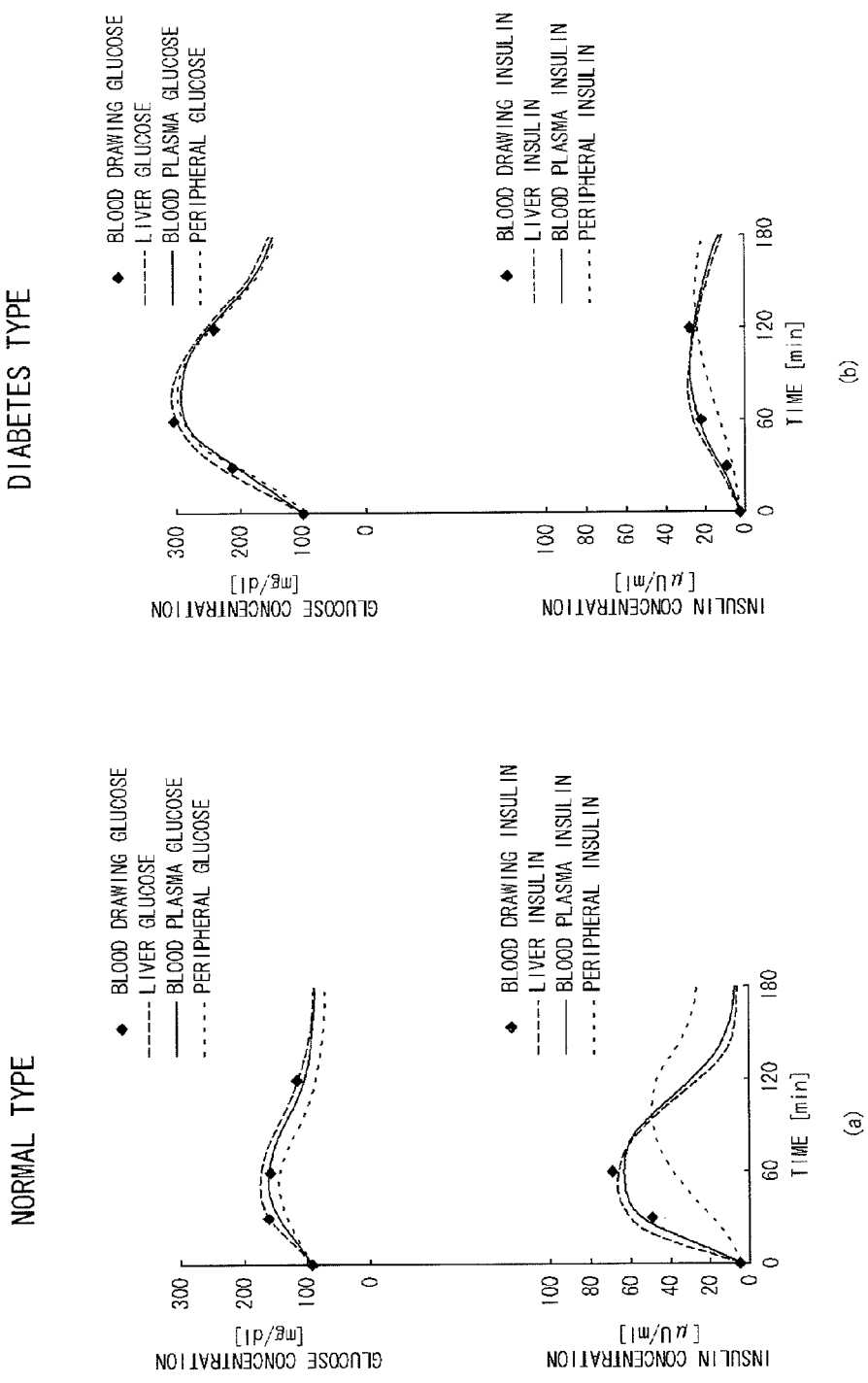
FIG. 8 is a graph showing a glucose concentration and an insulin concentration which are outputted from the biological model.
Figure 9:
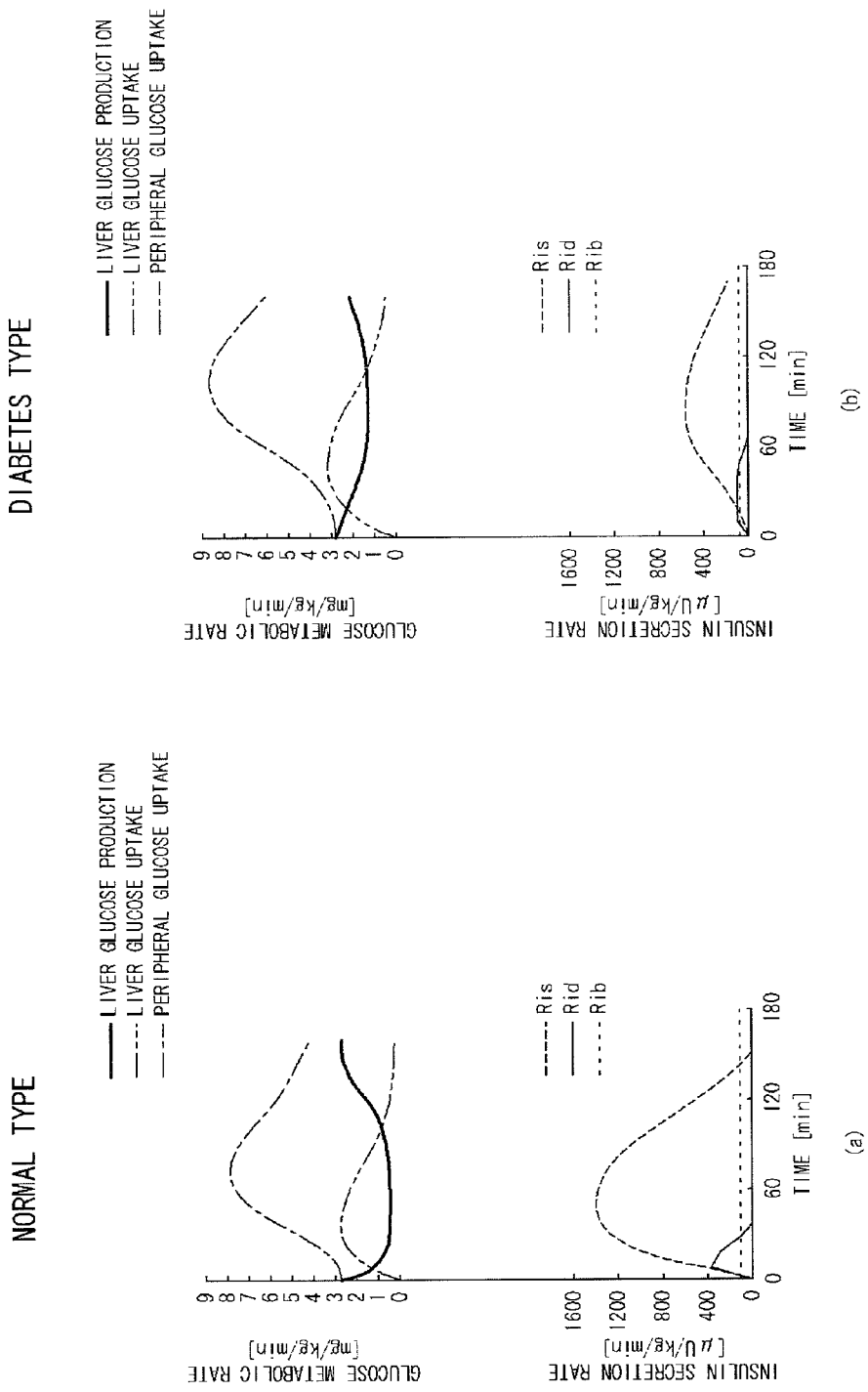
FIG. 9 is a graph showing insulin secretion rate and glucose metabolic rate which are outputted from the biological model.

FIGS. 8 and 9 are graphs showing values outputted from the biological model M which is generated as described above. Here, the graphs of FIGS. 8 and 9 may be outputted by a display device 120 and outputted into a paper medium by a printer and others. Therefore, it is possible to support doctor's diagnostic care by these outputs.

FIG. 8 represents the liver glucose concentration G1(t), the blood plasma glucose concentration G2(t), the peripheral glucose concentration G3(t), the liver insulin concentration I1(t), the blood plasma insulin concentration I2(t), and the peripheral insulin concentration I3(t) which are outputted from the generated biological model M as well as the blood drawing glucose concentration G2_ref(t) and the blood drawing insulin concentration I2_ref(t) which are actual values.

Further, FIG. 8(a) shows output of the biological model generated so as to adapt to a normal-type patient who does not have diabetes. FIG. 8(b) shows output of the biological model generated so as to adapt to the patient who has diabetes. Here, in FIGS. 8 and 9, the variable parameter of the normal-type biological model is adjusted to Sis=21.2, Sid=122.7, τis=4.7, a01=75.6, Spgu=10.4, and the variable parameter of the diabetic-type biological model is adjusted to Sis=3.1, Sid=24, τis=19.2, a01=84.7, Spgu=12.9.

As shown in FIG. 8, the actual measurement values (blood drawing glucose concentration and blood drawing insulin concentration) is fully matched with the blood plasma glucose concentration and the blood plasma insulin concentration of the biological model M. Further, temporal variation of not only the blood plasma glucose concentration and the blood plasma insulin concentration but also the liver glucose concentration, the peripheral glucose concentration, the liver insulin concentration, and the peripheral insulin concentration is outputted. Therefore these concentrations are enabled to be grasped by a system user and useful as diagnostic support information.

FIG. 9 shows the insulin secretion rate Ris(t) depending on the liver glucose production rate Rg20(t), the liver glucose uptake rate Rg01(t), the peripheral glucose uptake rate PGU (t), and the insulin secretion rate calculated by the generated biological model M, the insulin secretion rate Rid(t) depending on temporal variation of the glucose concentration G2(t), and the fasting insulin production rate preset biological model M Rib(t) which is set beforehand by the generated biological model M.

Further FIG. 9(a) shows the value of the biological model generated so as to adapt to the normal-type patient. FIG. 9(b) shows the value of the biological model generated so as to adapt to the diabetic patient. FIG. 8(b) and FIG. 9(b) are based on the biological model of the same patient.

The behavior of the diabetic-type case exemplified in FIG. 9(b) is enabled to understand by comparison with the normal-type case of FIG. 9(b). In the case of FIG. 9(b) based on comparison between both, it is found that the insulin secretion is low (Rid(t) and Ris(t)). Especially it is found that the secretion in time range (up to one hour) early stage after glucose tolerance is low. Therefore, the peripheral glucose uptake rate Rg03(t) at an early stage after glucose tolerance is low and the liver glucose production rate Rg20(t) is not fully inhibited.

Therefore, it is estimated that low pancreas insulin secretion is a main factor of high blood glucose level after meal.

Back to FIG. 5, using the generation model M generated to the individual patient and inputted medical data, a pathological condition estimation unit 133a of the diagnostic support information generation unit 133 analyzes diabetes pathological conditions in view of insulin secretion deficiency, peripheral insulin resistance, and increased liver glucose release. A pathological condition classification unit 133b classifies pathological conditions based on the estimated pathological conditions and generates diagnostic support information.

Figure 10:
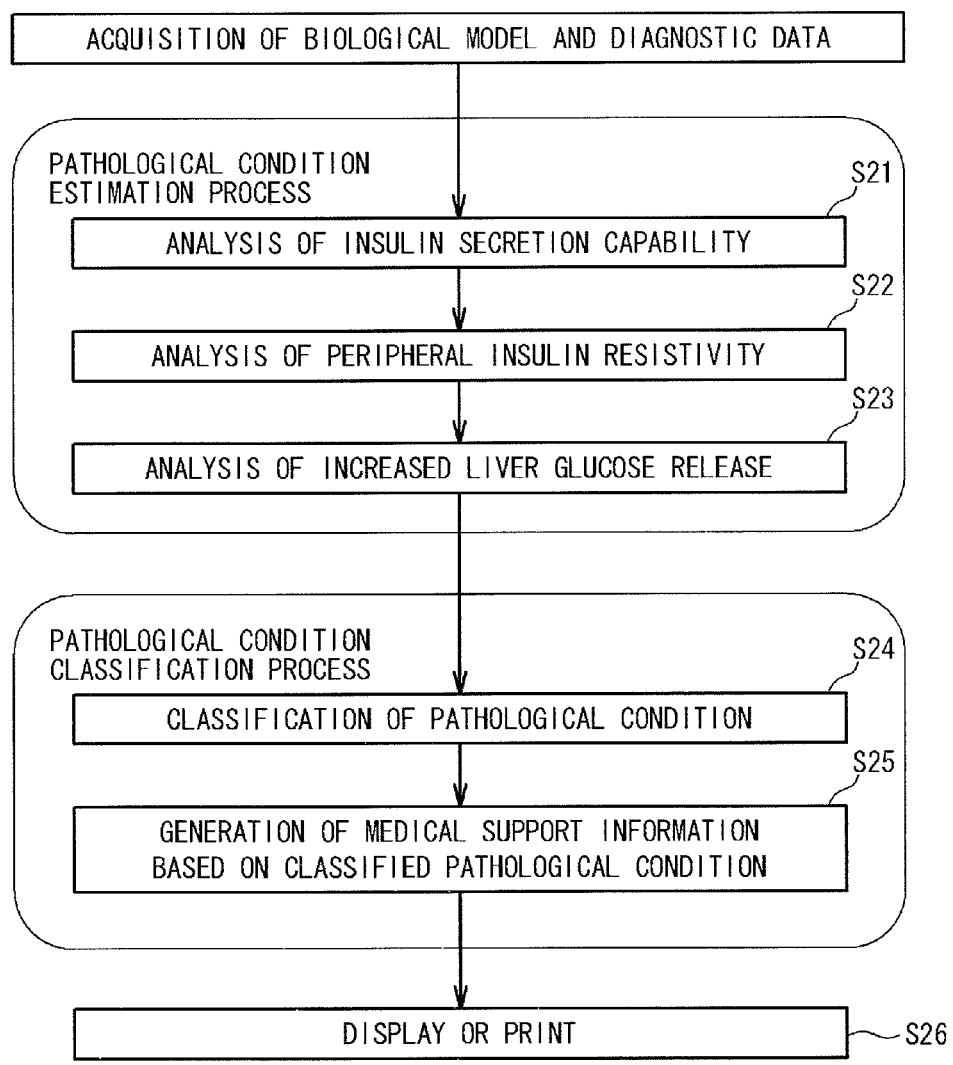
FIG. 10 is a flowchart showing diagnostic support information generation and an output process.

FIG. 10 shows a pathological condition estimation process and a pathological condition classification process by the diagnostic support information generation unit 133. The diagnostic support information generation unit 133 first acquires the biological model M and the diagnostic data which are memorized in the memory device.

Then, the pathological condition estimation unit 133a analyses on the insulin secretion deficiency, the peripheral insulin resistance, and the increased liver glucose release (Steps S21, S22, and S23). Specifically, it computes index for pathological condition analysis from the above view points based on respective values of the biological model M and the inputted diagnostic data. As the index, examples are "basic secretion", "secretion quantity", "secretion sensitivity", "peripheral glucose uptake", "peripheral sensitivity", "liver glucose uptake", and "liver glucose production".

Here, "basic secretion" is a fasting insulin secretion quantity and calculated from fasting blood plasma insulin concentration I2(t=0) being a variable of the biological model M. "Secretion quantity" is a total insulin secretion quantity in OGTT and calculated from an integration value of blood plasma insulin concentration I2(t) of the biological model M. "Secretion sensitivity" is blood-glucose dependent insulin secretion sensitivity and calculated from the insulin secretion sensitivity Sis depending on the glucose concentration being a variable parameter of the biological model M.

"Peripheral glucose uptake" is a variation of the total peripheral glucose uptake quantity in OGTT and calculated from an integration value of peripheral glucose uptake rate Rg03(t) being a variation of the biological model M. Here, Rg03(t) is calculated based on the peripheral glucose concentration G3(t), the peripheral insulin concentration I3(t), and the peripheral glucose uptake sensitivity Spgu being a variable parameter. "Peripheral sensitivity" is a peripheral insulin sensitivity and calculated from the peripheral glucose uptake sensitivity Spgu being a variable parameter of the biological model M. "Liver glucose uptake" is the total liver glucose uptake quantity in OGTT and calculated from an integration value of the liver glucose uptake rate Rg01(t) being a variation of the biological model M. Here, the liver glucose uptake rate Rg01 is a value calculated based on the liver glucose concentration G1(t) and the variable parameter a01. "Liver glucose production" is the total liver glucose production quantity in OGTT and calculated from an integration value of the liver glucose production rate Rg20(t) being a variation of the biological model M. Here, the liver glucose production rate Rg20(t) is a value calculated based on the liver insulin concentration I1(t).

The above-described indexes are all obtainable from internal information of the generated biological model M or the actual measurement value. As shown in FIG. 11 described later, respective indexes are standardized for intuitively imagining pathological conditions according to the present embodiment. In the present embodiment, patient's pathological conditions represented by using these indexes are referred to as "pathological condition profile". Here, the index indicative of pathological conditions is not limited to the above but the other index may be used as necessary.

Subsequently, the pathological condition classification unit 133b classifies pathological conditions based on an estimated pathological condition profile (Step S24). As examples of classification of the pathological conditions, they may be "normal", "insulin secretion deficiency type", "slight insulin secretion deficiency type", and "insulin resistivity type" as shown in FIG. 11. Further, as examples of the other classification, they may be classified into groups adaptable for respective medicines such as "sulfonylurea drug type", "glinide type", "thiazolidine derivative drug type" "biguanide drug type".

For classifying the pathological conditions based on the pathological condition profile, results of pathological condition classification by medical specialists with respect to various pathological condition profiles are previously built up as database, and the pathological condition classification unit 133b may select the classification result of the medical specialist to which the pathological condition profile of the subject patient resemble most on the database. Further, predetermined classification criteria are preset based on respective index values included in the pathological condition profile, and the pathological conditions may be classified based on thus classification criteria. Further, the pathological conditions may be classified by using a medicinal effect prediction result employing the biological model, such as pseudo-improvement of a parameter of the biological model corresponding to an action site of medicine. Thus a method of the pathological condition classification is not especially limited.

The pathological conditions and the pathological condition profile which are classified as described above are stored in the memory device as diagnostic support information (Step S25). The generated diagnostic support information includes information useful for diagnostic support such as recommended prescription medicine in response to the pathological condition classification.

The diagnostic support information generated as described above (may include information shown in FIGS. 8 and 9) is outputted by the diagnostic support information output unit 134 through the display device and the printer (Step S26). Therefore, it is possible that the system user (doctor) obtains information useful for the diagnostic care of the diabetes patient.

The present invention is not limited to the above-described embodiment but various modifications are available. For example, in the above embodiment, although a single computer performs processes with regard to generation of a biological model, and generation and output of diagnostic support information, the present invention is not limited to this. It is also possible to employ a distributed system in which the above processes are performed distributively with a plurality of devices (computers).

The invention claimed is:
1. A diagnostic support apparatus for diabetes comprising
an input interface configured to receive an input of a laboratory value comprising a glucose concentration and an insulin concentration in a blood collected from a patient,
a processor, and a memory that stores a biological model, which describes organ functions related to diabetes as a mathematical model which has a plurality of parameters, and which is divided into an insulin kinetic unit showing an insulin flow and a glucose kinetic unit showing a glucose flow, wherein the processor is programmed to:
  adjust values of parameters of the insulin kinetic unit until a blood plasma insulin concentration output from the insulin kinetic unit are substantially matched with the insulin concentration included in the laboratory value so that the insulin kinetic unit is adapted to the patient;
  adjust values of parameters of the glucose kinetic unit until a blood plasma glucose concentration output from the glucose kinetic unit are substantially matched with the glucose concentration included in the laboratory value so that the glucose kinetic unit is adapted to the patient; and
  output indexes representing pathological conditions of the patient based on the adjusted values of the parameters of the insulin kinetic unit and the adjusted values of the parameters of the glucose kinetic unit,
wherein the biological model includes organ blocks comprising:
  a liver block which represents an interstitial fluid in a liver and a function of glucose uptake and glucose production in the liver,
  a peripheral tissue block which represents an interstitial fluid in a peripheral tissue and a function of glucose uptake in the peripheral tissue,
  a blood plasma block which represents a blood plasma in a blood vessel existing between the liver and the peripheral tissue,
wherein the biological model is programmed such that a transfer of glucose and insulin in an interstitial fluid and blood plasma accompanying a blood circulation is represented in the liver block, the peripheral tissue block and the blood plasma block,
wherein an inflow and an outflow of the glucose are reciprocally produced between the liver block and the blood plasma block in the glucose kinetic unit, and an inflow and an outflow of the glucose are reciprocally produced between the blood plasma block and the peripheral tissue block in the glucose kinetic unit,
wherein an inflow and an outflow of the insulin are reciprocally produced between the liver block and the blood plasma block in the insulin kinetic unit, and an inflow and an outflow of the insulin are reciprocally produced between the blood plasma block and the peripheral tissue block in the insulin kinetic unit,
wherein each of the liver block, the peripheral tissue block and the blood plasma block in the glucose kinetic unit calculates at least one of a cumulative quantity and a concentration of the glucose in each block based on a quantity of inflow and outflow of the glucose in each block in the glucose kinetic unit and a quantity of at least one of an increase and a decrease of glucose in each block in the glucose kinetic unit due to the respective function of each block respectively,
wherein each of the liver block, the peripheral tissue block and the blood plasma block in the insulin kinetic unit calculates at least one of a cumulative quantity and a concentration of the insulin in each block, based on a quantity of inflow and outflow of the insulin in each block in the insulin kinetic unit and a quantity of at least one of an increase and a decrease of insulin in each block in the insulin kinetic unit due to the respective function of each block, respectively, and
wherein the processor is further programmed to generate and output diagnostic support information of the patient comprising the indexes based on at least one of: the calculated cumulative quantity and the concentration of the glucose in each of the liver block, the peripheral tissue block and the blood plasma block in the glucose kinetic unit, and the calculated cumulative quantity and the concentration of insulin in each of the liver block, the peripheral tissue block, and the blood plasma block in the insulin kinetic unit.

2. The diagnostic support apparatus for diabetes of claim 1, wherein
  the intestine block is provided with a glucose tolerance quantity in the glucose tolerance test as an exogenous glucose quantity from outside of the biological model; and
  the intestine block calculates an exogenous glucose inflow rate provided to the liver block based on the exogenous glucose quantity.

3. The diagnostic support apparatus for diabetes of claim 1, wherein
  the pancreas block determines a secretion quantity of insulin flowing into the liver block, based on the glucose concentration in the blood and temporal variation of the glucose concentration in the blood.

4. The diagnostic support apparatus for diabetes of claim 1, wherein
  the generating the diagnostic support information by the processor comprises generating the indexes which are medical tools for analyzing the pathological conditions of the patient, based on the cumulative quantity and the concentration of glucose in each of the liver block, the peripheral tissue block and the blood plasma block and at least one of a cumulative quantity and a concentration of insulin in each of the liver block, the peripheral tissue block and the blood plasma block.

5. The diagnostic support apparatus for diabetes of claim 4, wherein
  the processor is further programmed to classify the pathological condition of the patient based on the generated index.

6. The diagnostic support apparatus for diabetes of claim 1, wherein
  the liver block calculates at least one of a value indicating a function of liver glucose uptake and a value indicating a function of liver glucose production in the liver block based on at least one of the cumulative quantity and the concentration of glucose in the liver block, and calculates at least one of the cumulative quantity and the concentration of glucose in the liver block while calculating variation of at least one of the cumulative quantity and the concentration of glucose by at least one of the function of the liver glucose uptake and the function of the liver glucose production.

7. The diagnostic support apparatus for diabetes of claim 1, wherein
  the peripheral tissue block calculates a value indicating a function of peripheral glucose uptake in the peripheral tissue block based on the cumulative quantity or the concentration of glucose in the peripheral tissue block, and calculates the cumulative quantity or the concentration of glucose in the peripheral tissue block while calculating variation of the cumulative quantity or the concentration of glucose by the function of the peripheral glucose uptake.

8. A non-transitory computer-readable storage medium which stores programs executable by a processor to control a memory storing a biological model, which describes organ functions related to diabetes as a mathematical model which has a plurality of parameters, and which is divided into an insulin kinetic unit showing an insulin flow and a glucose kinetic unit showing a glucose flow,
   wherein an input of a laboratory value is received comprising a glucose concentration and an insulin concentration in a blood collected from a patient,
   wherein the programs cause the processor to:
      adjust values of parameters of the insulin kinetic unit until a blood plasma insulin concentration output from the insulin kinetic unit are substantially matched with the insulin concentration included in the laboratory value so that the insulin kinetic unit is adapted to the patient; and
      adjust values of parameters of the glucose kinetic unit until a blood plasma glucose concentration output from the glucose kinetic unit are substantially matched with the glucose concentration included in the laboratory value so that the glucose kinetic unit is adapted to the patient; and
      output indexes representing pathological conditions of the patient based on the adjusted values of the parameters of the insulin kinetic unit and the adjusted values of the parameters of the glucose kinetic unit,
   wherein the biological model includes organ blocks comprising:
      a liver block which represents an interstitial fluid in a liver and a function of glucose uptake and glucose production in the liver,
      a peripheral tissue block which represents an interstitial fluid in a peripheral tissue and a function of glucose uptake in the peripheral tissue, and
      a blood plasma block which represents a blood plasma in a blood vessel existing between the liver and the peripheral tissue,
   wherein the biological model is programmed such that a transfer of glucose and insulin in an interstitial fluid and blood plasma accompanying a blood circulation is represented in the liver block, the peripheral tissue block and the blood plasma block,
   wherein an inflow and an outflow of the glucose are reciprocally produced between the liver block and the blood plasma block in the glucose kinetic unit, and an inflow and an outflow of the glucose are reciprocally produced between the blood plasma block and the peripheral tissue block in the glucose kinetic unit,
   wherein an inflow and an outflow of the insulin are reciprocally produced between the liver block and the blood plasma block in the insulin kinetic unit, and an inflow and an outflow of the insulin are reciprocally produced between the blood plasma block and the peripheral tissue block in the insulin kinetic unit,
   wherein each of the liver block, the peripheral tissue block and the blood plasma block in the glucose kinetic unit calculates at least one of a cumulative quantity and a concentration of the glucose in each block based on a quantity of inflow and outflow of the glucose in each block in the glucose kinetic unit and a quantity of at least one of an increase and a decrease of glucose in each block in the glucose kinetic unit due to the respective function of each block, respectively,
   wherein each of the liver block, the peripheral tissue block and the blood plasma block in the insulin kinetic unit calculates at least one of a cumulative quantity and a concentration of the insulin in each block, based on a quantity of inflow and outflow of the insulin in each block in the insulin kinetic unit and a quantity of at least one of an increase and a decrease of insulin in each block in the insulin kinetic unit due to the respective function of each block, respectively, and
   wherein the programs further cause the processor to generate and output diagnostic support information of the patient comprising the indexes based on at least one of: the calculated cumulative quantity and the concentration of the glucose in each of the liver block, the peripheral tissue block and the blood plasma block in the glucose kinetic unit, and the calculated cumulative quantity and the concentration of insulin in each of the liver block, the peripheral tissue block, and the blood plasma block in the insulin kinetic unit.

9. The non-transitory computer-readable storage medium of claim 8, wherein
   the biological model is provided with a glucose tolerance quantity in the glucose tolerance test as an exogenous glucose quantity from outside of the biological model; and
   the intestine block calculates an exogenous glucose inflow rate provided to the liver block based on the exogenous glucose quantity.

10. The non-transitory computer-readable storage medium of claim 8, wherein
    the liver block calculates at least one of a value indicating a function of liver glucose uptake and a value indicating a function of liver glucose production in the liver block based on at least one of the cumulative quantity and the concentration of glucose in the liver block, and calculates at least one of the cumulative quantity and the concentration of glucose in the liver block while calculating variation of at least one of the cumulative quantity and the concentration of glucose by at least one of the function of the liver glucose uptake and the function of the liver glucose production.

11. The non-transitory computer-readable storage medium of claim 8, wherein
    the peripheral tissue block calculates a value indicating a function of peripheral glucose uptake in the peripheral tissue block based on the cumulative quantity or the concentration of glucose in the peripheral tissue block, and calculates the cumulative quantity or the concentration of glucose in the peripheral tissue block while calculating variation of the cumulative quantity or the concentration of glucose by the function of the peripheral glucose uptake.

12. The diagnostic support apparatus for diabetes of claim 1, wherein the glucose kinetic unit further comprises an intestine block which represents a function of glucose absorption in an intestine and wherein the intestine block flows glucose out to the liver block according to a quantity of glucose orally administered to the patient.

13. The diagnostic support apparatus for diabetes of claim 1, wherein the insulin kinetic unit further comprises a pancreas block which represents a function of insulin secretion in a pancreas and wherein the pancreas block flows insulin out to the liver block according to a glucose concentration collected from the patient.

14. The diagnostic support apparatus for diabetes of claim 1, wherein the processor is further configured to output to a display an analysis result in a form of a figure indicating basic secretion, secretion quantity, liver glucose uptake quantity, liver glucose production quantity, peripheral tissue sensitivity, a peripheral glucose uptake quantity of the patient, based on the generated diagnostic support information.

15. The diagnostic support apparatus for diabetes of claim 1, wherein the processor is further configured to output to a display a drug recommendation for the patient based on the generated diagnostic support information.

* * * * *